United States Patent [19]

Festal et al.

[11] Patent Number: 5,338,849

[45] Date of Patent: Aug. 16, 1994

[54] AZAINDOLES, PREPARATION PROCESSES AND MEDICINAL PRODUCTS CONTAINING THEM

[75] Inventors: Didier Festal, Ecully; Denis Descours, Villeurbanne; Jacques Decerprit, Miribel, all of France

[73] Assignee: Lipha, Lyonnaise Industrielle Pharmaceutique, Lyon, France

[21] Appl. No.: 13,427

[22] Filed: Feb. 4, 1993

[30] Foreign Application Priority Data

Feb. 14, 1992 [FR] France ................. 92 01701

[51] Int. Cl.$^5$ ................ C07D 471/04; A61K 31/405; A61K 31/44
[52] U.S. Cl. ................................. 546/113
[58] Field of Search ................ 546/113; 514/300

[56] References Cited

FOREIGN PATENT DOCUMENTS

| | | |
|---|---|---|
| 659467 | 8/1965 | Belgium . |
| 0265640 | 5/1988 | European Pat. Off. . |
| 0279263 | 8/1988 | European Pat. Off. . |
| 0415413 | 3/1991 | European Pat. Off. . |
| 0465970 | 1/1992 | European Pat. Off. . |
| 0506532 | 9/1992 | European Pat. Off. . |
| 1261179 | 9/1961 | France . |
| WO91/04027 | 4/1991 | PCT Int'l Appl. . |

OTHER PUBLICATIONS

CA 118(7):59851y of EP506532 published Sep. 30, 1992 by Festal et al.

Goodman and Gilman's *The Pharmacological Basis of Therapeutics* eighth edition, 1990, pp. 882 and 887.

*Primary Examiner*—C. Warren Ivy
*Assistant Examiner*—D. Margaret M. Mach
*Attorney, Agent, or Firm*—Oblon, Spivak, McClelland, Maier & Neustadt

[57] ABSTRACT

These compounds correspond to the formula

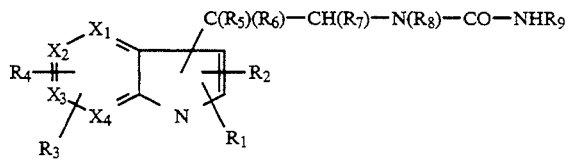

in which
- one of the groups $X_1$ to $X_4$ represents nitrogen and the others a CH radical,
- $R_1$ and $R_2$ represent H, halogen, alkyl, hydroxymethyl, alkyloxymethyl, dialkylaminoalkyl, dialkylaminoalkyloxymethyl, carboxyl, ethyl carboxylate, piperidino, alkenyl, cycloalkyl, cycloalkenyl, alkylthio, benzyl, phenyl, thiophene or pyridine, optionally substituted,
- $R_3$ and $R_4$ represent H, halogen, alkyl, cycloalkyl, alkoxy or alkylthio,
- $R_5$ and $R_6$ denote H, alkyl, alkenyl, cycloalkyl, cycloalkenyl, alkoxyalkyl or alkylthioalkyl, or together form alkylene or alkyleneoxyalkylene chains,
- $R_7$ denotes H, alkyl or cycloalkyl; one of the radicals $R_5$ to $R_7$ can also denote optionally substituted phenyl or benzyl,
- $R_8$ represents H, alkyl, cycloalkyl or optionally substituted phenyl or benzyl,
- $R_9$ denotes optionally substituted phenyl, naphthyl or heterocyclic, as well as their tautomeric forms, processes for preparing them and application as hypolipidaemic and antiatheromatous medicinal products.

12 Claims, No Drawings

AZAINDOLES, PREPARATION PROCESSES AND MEDICINAL PRODUCTS CONTAINING THEM

The present invention relates to new azaindole compounds, the processes for preparing these compounds, to pharmaceutical compositions containing them and to their use as medicinal products, in particular in the treatment of hyperlipidaemia and atherosclerosis.

Lipid deposits, in particular deposits of cholesterol in the vessels, are known to be the source of the formation of atheromatous plaques, which are the cause of miscellaneous cardiovascular diseases; more precisely, atheroma is a form of atherosclerosis which is characterised by an excessive accumulation of lipids, especially cholesterol esters, in the wall of the vessels; it was recently found that an enzyme, acylcoenzyme A: cholesterol acyltransferase (ACAT), was responsible for the esterification of cholesterol, and a correlation was demonstrated between an increase in the activity of this enzyme and the accumulation of esters in the vascular wall; it is also known that dietary cholesterol is absorbed in free form and is then esterified by intestinal ACAT and released into the bloodstream in the form of VLDL and/or chylomicra.

It has been sought to develop products that inhibit ACAT and are capable of preventing the intestinal absorption of dietary and biliary cholesterol and of combating the deposition of cholesterol esters in the wall of the vessels.

This search for ACAT inhibitors led the inventors to develop a new family of azaindoles, and to find that these products unexpectedly manifest a potent inhibitory activity with respect to vascular and intestinal ACAT, associated with an intense anti-hyperlipidaemic effect in various animal species.

These properties of the compounds of the invention make them especially useful, in particular, for the treatment of hyperlipidaemia and atherosclerosis.

The invention relates more especially to the compounds of formula 1 below:

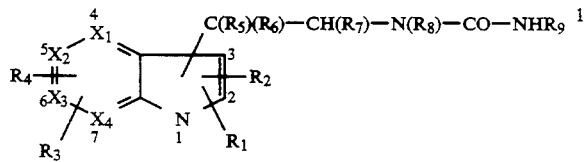

in which
one of the groups $X_1$ to $X_4$ denotes a nitrogen atom and the others represent a CH radical;

$R_1$ and $R_2$, which may be located at position 1, 2 or 3 of the azaindole ring-system, independently represent a hydrogen atom or linear or branched $C_1$ to $C_{12}$ alkyl radicals or $C_2$ to $C_6$ alkenyl radicals optionally substituted at the $\omega$ position with a carboxyl, $C_1$ to $C_3$ alkyl carboxylate or phenyl radical; $R_1$ and $R_2$ can also represent $C_3$ to $C_8$ cycloalkyl or cycloalkenyl radicals or, when they are at position 2 or 3 of the azaindole ring-system, a halogen atom, in particular a chlorine or bromine atom, or a $C_1$ to $C_6$ alkylthio radical; $R_1$ and $R_2$ can also denote phenyl or benzyl groups, unsubstituted or bearing one to three substituents chosen from halogen and $C_1$ to $C_4$ alkyl, alkoxy and alkylthio radicals, or thienyl or pyridyl groups which can optionally bear a substituent chosen from halogen and $C_1$ to $C_4$ alkyl and alkoxy radicals; one of $R_1$ and $R_2$ can also denote hydroxymethyl, ($C_1$ to $C_4$ alkoxy)methyl, N,N-di($C_1$ to $C_4$ alkyl)amino($C_1$ to $C_4$ alkyl)oxymethyl, carboxyl, $C_1$ to $C_3$ alkyl carboxylate or piperidino radicals and the other a hydrogen atom;

$R_3$ and $R_4$, which may be located on the vertices 4, 5, 6 or 7 of the azaindole ring-system provided that these vertices embody a carbon atom, each represent a hydrogen or halogen atom, more especially bromine or chlorine, or represent $C_1$ to $C_6$ alkyl, alkoxy or alkylthio or $C_3$ to $C_8$ cycloalkyl radicals;

the group $-C(R_5)(R_6)-CH(R_7)-N(R_8)-CO-NH-R_9$ may be attached to the vertices 1, 2 or 3 of the azaindole ring-system, on the understanding that, when the nitrogen atom at position 1 of the azaindole ring-system is not substituted with one of the groups $R_1$, $R_2$ or $-C(R_5)(R_6)-CH(R_7)-N(R_8)CO-NH-R_9$, it bears a hydrogen atom;

$R_5$ and $R_6$ each represent a hydrogen atom or represent $C_1$ to $C_{12}$ alkyl, $C_2$ to $C_5$ alkenyl, $C_3$ to $C_8$ cycloalkyl or cycloalkenyl or $C_2$ to $C_{12}$ alkoxyalkyl or alkylthioalkyl radicals, or alternatively $R_5$ and $R_6$ together form an alkylene chain of formula $-(CH_2)_p-$ optionally substituted with one or two $C_1$ to $C_4$ alkyl radicals and in which p can assume the values 3 to 7, or an alkyleneoxyalkylene chain of formula $-(CH_2)_x-O-(CH_2)_y-$ in which x and y can independently assume the value 1 or 2;

$R_7$ denotes a hydrogen atom or a $C_1$ to $C_6$ alkyl or $C_3$ to $C_8$ cycloalkyl radical;

one of the substituents $R_5$ to $R_2$ can also represent a phenyl or benzyl radical, unsubstituted or bearing one to three substituents chosen from halogen and $C_1$ to $C_4$ alkyl, alkoxy and alkylthio radicals;

$R_8$ denotes a hydrogen atom, a linear or branched $C_1$ to $C_{12}$ alkyl radical, a $C_3$ to $C_8$ cycloalkyl radical or a benzyl radical which is unsubstituted or bears 1 to 3 substituents chosen from halogen and $C_1$ to $C_4$ alkyl, alkoxy or alkylthio radicals;

$R_9$ denotes a phenyl radical, unsubstituted or bearing 1 to 3 substituents chosen from halogen and $C_1$ to $C_4$ alkyl, alkoxy and alkylthio radicals; or alternatively $R_9$ represents a 1- or 2-naphthyl radical or a 5- or 6-membered heterocyclic radical containing one or two hetero atoms chosen from sulphur, oxygen or nitrogen, optionally fused with a benzene ring and, where appropriate, substituted with one or two halogen atoms or $C_1$ to $C_4$ alkyl or alkoxy radicals.

According to a preferred form of the invention, the subject of the latter is the compounds of formula 1 in which $R_1$ and $R_2$ independently represent hydrogen or halogen atoms or alkyl, phenyl or benzyl radicals, $R_3$ and $R_4$ represent hydrogen or halogen atoms or $C_1$ to $C_6$ alkyl or alkoxy radicals, $R_5$ and $R_6$ represent hydrogen or halogen atoms or $C_1$ to $C_6$ alkyl or alkoxy or $C_2$ to $C_6$ alkenyl radicals, or together form a $C_4$ alkylene chain, $R_7$ represents a hydrogen atom, $R_8$ represents a hydrogen atom or a $C_1$ to $C_8$ alkyl radical and $R_9$ denotes a phenyl group unsubstituted or bearing one to three substituents chosen from halogen and $C_1$ to $C_4$ alkyl and alkoxy radicals.

The term "alkyl" is understood to mean a hydrocarbon arrangement which, except where otherwise stated, is saturated, linear or branched and derived from the corresponding alkane by elimination of a hydrogen atom, and comprises, more especially, 1 to 5 carbon atoms, such as, for example: methyl, ethyl, n-propyl, n-butyl, 2-methylethyl, 2,2-dimethylethyl or 3,3-dimethylpropyl.

The term "alkenyl" is understood to mean a hydrocarbon arrangement which, except where otherwise stated, is linear or branched, comprises, more specifically, 3 to 6 carbon atoms and contains a double bond, such as, for example: 2-propenyl, 2-methyl-2-propenyl, 3-butenyl.

The term "halogen" is understood, more specifically, to mean bromine, chlorine or fluorine.

The term "N,N-dialkylamino" characterises an arrangement comprising a nitrogen atom substituted with alkyl radicals such as are defined above, the free valency of which effects the attachment to the parent molecule.

The term "N,N-dialkylaminoalkyl" denotes an alkyl radical as defined above, substituted at the $\omega$ position with an N,N-dialkylamino radical as defined above.

The term "N,N-dialkylaminoalkoxymethyl" characterises an N,N-dialkylaminoalkyl radical as defined above, linked to a methyl radical via an oxygen atom, such as, for example: N,N-dimethylaminoethyloxy.

The terms "alkoxy" or "alkylthio" characterise an alkyl arrangement as defined above, attached to the parent molecule through an oxygen or sulphur atom, such as, for example, the radicals: methoxy, ethoxy, n-propoxy, 1-methylethoxy, n-butoxy, 1,1-dimethylethoxy, methylthio, ethylthio, n-propylthio or 1-methylethylthio.

The terms "alkoxyalkyl" or "alkylthioalkyl" are understood to mean an alkoxy or alkylthio arrangement as defined above, attached to the parent molecule via a 10 linear alkyl radical such as is defined above, such as, for example: methoxymethyl, methoxyethyl, 2-methylethoxymethyl, methylthiomethyl, ethylthiomethyl.

The term "cycloalkyl" characterises a saturated, cyclic hydrocarbon arrangement derived from a cyclane such as cyclopropane, cyclopentane, cyclohexane, cycloheptane or cyclooctane by elimination of a hydrogen atom and, where appropriate, substituted with one or two alkyl radicals such as are defined above, such as, for example: 2-methylcyclopentyl, 2-methylcyclohexyl, 4,4-dimethylcyclohexyl.

The term "cycloalkenyl" characterises a cycloalkyl radical as defined above and containing a double bond.

"5- or 6-membered heterocyclic radical containing 1 or 2 hetero atoms" is understood to mean a radical derived, by elimination of a hydrogen atom, from a 5- or 6-membered ring having a maximum degree of unsaturation and containing one or two hetero elements chosen from oxygen, nitrogen or sulphur, such as, for example, thiophene, furan, pyrrole, pyridine, thiazole, isothiazole, oxazole, isoxazole, imidazole, pyrimidine or pyrazine rings, in particular 2- or 3-thienyl or -furyl, 1-pyrrolyl, 2-, 4- or 5-oxazolyl, -thiazolyl or -imidazolyl, 3-, 4- or 5-isoxazolyl or -isothiazolyl, 2-, 3-or 4-pyridyl, 2-or 5-pyrimidinyl or 2-or 3-pyrazinyl radicals; the expression "optionally fused with a benzene ring" characterises radicals derived, by elimination of a hydrogen atom, from the bicyclic systems resulting from the fusion of the abovementioned heterocycles with a benzene ring, such as the bicyclic systems: benzothiophene, benzofuran, indole, benzimidazole, quinoline, isoquinoline, quinoxaline or quinazoline, especially benzo[b]thien-5- or -6-yl or benzo[b]furan-5- or -6-yl, 2-, 3-, 5-or 6-indolyl, 2-, 5-or 6-benzimidazolyl, 2-, 3-, 4-, 5-, 6- or 7-quinolyl, 1-, 3-, 4-, 6- or 7-isoquinolyl, 2-, 3-, 6-or 7-quinoxalinyl or 2-, 4-, 6- or 7-quinazolinyl radicals.

The compounds of formula I can contain one or more asymmetric centres, in particular when the substituents $R_5$, $R_6$ and $R_7$ are different, thereby giving rise to diastereoisomers, enantiomers and racemates which also form part of the invention.

It falls within the normal competence of the expert to isolate or synthesise an optically active form of a compound of formula 1, for example by resolution of a racemate or by synthesis starting from an optically active compound, and to determine the biological properties of the isomers thereby isolated according to the experiments described below.

The mixtures of stereoisomers may be separated by standard methods at whichever stage of the synthesis is most suitable; standard methods are understood to mean the collective processes familiar to the expert, such as, for example, crystallisation, chomatography or the formation of combinations with optically active compounds.

The compounds of formula 1 can exist in one or more tautomeric forms which also form part of the invention.

As specific compounds of the invention, there may be mentioned, solely by way of example, the following compounds whose structural formulae appear in the attached drawings:

compound no. 1: $N^1$-[1-(7-azaindol-1-yl)cyclopentylmethyl]-$N^2$-(2,6-diisopropylphenyl)urea;

compound no.2: $N^1$-[2-(7-azaindol-1-yl)-2-allyl-4-pentenyl]-$N^2$-(2,6-diisopropylphenyl)urea;

compound no.3: $N^1$-[2-(7-azaindol-1yl)-2-allyl-4-pentenyl]-$N^2$-(4-fluoro-2-methylphenyl)urea;

compound no.4: $N^1$-[2-(7-azaindol-1-yl)-2-phenethyl]-$N^2$-(2,6-diisopropylphenyl)urea;

compound no.5: $N^1$-[2-(7-azaindol-1-yl)-2-methylpropyl]-$N^2$-(2,6-diisopropylphenyl)urea;

compound no.6: $N^1$-[(1-methyl-7-azaindol-3-yl)-cyclopentylmethyl]-$N^2$-(2,6-diisopropylphenyl)urea;

compound no.7: $N^1$-[(5-aza-indol-1-yl)cyclopentylmethyl]-$N^2$-(2,6-diisopropylphenyl)urea;

compound no.8: $N^1$-[2-(7-azaindol-1-yl)hexyl]-$N^2$-(2,6-diisopropylphenyl)urea;

compound no.9: $N^1$-[1-(3-ethyl-7-azaindol-1-yl)cyclopentylmethyl]-$N^2$-(2,6-diisopropylphenyl)urea;

compound no.10: $N^1$-[1-(7-azaindol-1-yl)cyclohexylmethyl]-$N^2$-(2,6-diisopropylphenyl)urea;

compound no.11: $N^1$-[1-(6-chloro-3-phenyl-7-azaindol-1-yl)cyclopentylmethyl]-$N^2$-(2,6-diisopropylphenyl)urea;

compound no.12: $N^1$-[2-(7-azoindol-1-yl)-3-phenylpropyl]-$N^2$-(2,6-diisopropylphenyl)-urea;

compound no.13: $N^1$-[1-(3-ethyl-4-azaindol-1-yl)cyclopentylmethyl]-$N^2$-(2,6-diisopropylphenyl)urea;

compound no.14: $N^1$-[4-(7-azaindol-1-yl)-4-pyranylmethyl]-$N^2$-(2,6-diisopropylphenyl)urea;

compound no.15: $N^1$-[4-(7-azaindol-1-yl)-1-pentenyl]-$N^2$-(2,6-diisopropylphenyl)urea;

compound no.16: $N^1$-[1-(2,3-dimethyl-7-azaindol-1-yl)-cyclopentylmethyl]-$N^2$-(2,6-diisopropylphenyl)urea;

compound no.17: $N^1$-[1-(3-benzyl-7-azaindol-1-yl)cyclopentylmethyl]-$N^1$-(2,6-diisopropylphenyl)urea;

compound no.18: $N^1$-[1-(3-butyl-7-azaindol-1-yl)cyclopentylmethyl]-$N^2$-(2,6-diisopropylphenyl)urea;

compound no.19: $N^2$[1-(3-propyl-azaindol-1-yl)cyclopentylmethyl]-$N^2$-(2,6-diisopropylphenyl)urea;

compound no.20: $N^1$-[1-(3-isopropyl-7-azaindol-1-yl)cyclopentylmethyl]-$N^2$-(2,6-diisopropylphenyl)urea;

compound no. 21 : $N^1$-[1-(3-phenyl-7-azaindol-1-yl)cyclopentylmethyl]-$N^2$-(2,6-diisopropylphenyl)urea;

compound no. 22: $N^1$-[2-(7-azaindol-1-yl)butyl]-$N^2$-(2,6-diisopropylphenyl)urea;

compound no.23: $N^1$-[1-(3-dimethylaminomethyl-2-azaindol-1-yl)cyclopentylmethyl]-$N^2$-(2,6-diisopropylphenyl)urea;

compound no. 24 : $N^1$-[1-(3-methylthio-7-azaindol-1-yl)cyclopentymethyl]-$N^2$-(2,6-diisopropylphenyl)urea;

compound no. 25: $N^1$-[1-(3-hydroxymethyl-7-azaindol-1-yl)cyclopentylmethyl]-$N^2$-(2,6-diisopropylphenyl)urea;

compound no. 26: $N^1$-[1-(5-chloro-3-ethyl-7-azaindol-1-yl)cyclopentylmethyl]-$N^2$-(2,6-diisopropylphenyl)urea compound no. 27: $N^1$-[1-(6-azaindol-1-yl)cyclopentylmethyl]-$N^2$-(2,6-diisopropylphenyl)urea;

compound no.28: $N^1$-[1-(4-methyl-3-phenyl-7-azaindol-1-yl)cyclopentylmethyl]-$N^2$-(2,6-diisopropylphenyl)urea;

compound no.29: $N^1$-[1-(3-methyl-7-azaindol-1-yl)cyclopentylmethyl]-$N^2$-(2,6-diisopropylphenyl)urea;

compound no.30: $N^1$-{1-[3-(4-fluorophenyl)-7-azaindol-1-yl]cyclopentylmethyl}-$N^2$-(2,6-diisopropylphenyl)urea;

compound no.31: $N^1$-[2-(3-phenyl-7-azaindol-1-yl)hexyl]-$N^2$-(2,6-diisopropylphenyl)urea;

compound no.32: $N^1$-{1-[3-(4-methoxyphenyl)-7-azaindol-1-yl]cyclopentylmethyl}-$N^2$-(2,6-diisopropylphenyl)urea;

compound no.33: $N^1$-[1-(3-methoxycarbonyl-7-azaindol-1-yl)cyclopentylmethyl]-$N^2$-(2,6-diisopropylphenyl)urea;

compound no.34: $N^1$-[1-(3-hexyl-7-azaindol-1-yl)cyclopentylmethyl]-$N^2$-(2,6-diisopropylphenyl)urea;

compound no.35: $N^1$-[1-(7-azaindol-1-yl)cyclopentylmethyl]-$N^2$-(2,4,6-trimethoxyphenyl)urea;

compound no. 36: $N^1$-[1-(7-azaindol-1-yl)cyclopentylmethyl]-$N^2$-(4,6-dimethoxy-5-pyrimidinyl)urea;

compound no.37: $N^1$-[1-(7-azaindol-1-yl)cyclopentylmethyl]-$N^2$-(2,6-diethylphenyl)urea;

compound no.38: $N^1$-[1-(7-azaindol-1-yl)cyclopentylmethyl]-$N^2$-(2-isopropylphenyl)urea;

compound no.39: $N^1$-[1-(7-azaindol-1-yl)cyclopentylmethyl]-$N^2$-(2,4-diisopropylphenyl)urea;

compound no.40: $N^1$-[1-(7-azaindol-1-yl)cyclopentylmethyl]-$N^1$-benzyl-$N^2$-(2,4-difluorophenyl)urea;

compound no.41: $N^1$-[1-(3-bromo-7-azaindol-1-yl)cyclopentylmethyl]-$N^2$-(2,6-diisopropylphenyl)urea;

compound no. 42: $N^1$-[1-(3-chloro-7-azaindol-1-yl)cyclopentylmethyl]-$N^2$-(2,6-diisopropylphenyl)urea;

compound no. 43: $N^1$-[1-(3-methoxymethyl-7-azaindol-1-yl)cyclopentylmethyl]-$N^2$-(2,6-diisopropylphenyl)urea;

compound no.44: $N^1$-{1-[3-(2-diethylaminoethoxymethyl)-7-azaindol-1-yl]cyclopentylmethyl}-$N^2$-(2,6-diisopropylphenyl)urea;

compound no.45: $N^1$-[1-(3-ethenyl-7-azaindol-1-yl)cyclopentylmethyl]-$N^2$-(2,6-diisopropylphenyl)urea;

compound no.46: $N^1$-{1-[3-(2-phenylethen-1-yl)-7-azaindol-1-yl]cyclopentylmethyl}-$N^2$-(2,6-diisopropylphenyl)urea;

compound no.47: $N^1$-{1-[3-(2-methoxycarbonylethen-1-yl)-7-azaindol-1-yl]cyclopentylmethyl}-$N^2$-(2,6-diisopropylphenyl)urea;

compound no.48: $N^1$-[1-(3-piperidino-7-azaindol-1-yl)cyclopentylmethyl]-$N^2$-(2,6-diisopropylphenyl)urea;

compound no.49: $N^1$-[(7-azaindol-1-yl)cyclopentylmethyl]-$N^2$-(2,6-diisopropylphenyl)urea hydrochloride;

compound no.50: $N^1$-[1-(7-azaindol-1-yl)cyclopentylmethyl]-$N^1$-benzyl-$N^2$-(2,6-diisopropylphenyl)urea;

compound no.51: $N^1$-[2-(3-ethyl-7-azaindol-1-yl)hexyl]-$N^2$-(2,6-diisopropylphenyl)urea hydrochloride.

The invention also relates to the processes for preparing the compounds of formula 1, characterised in that they entail at least as illustrated in the following scheme 1,

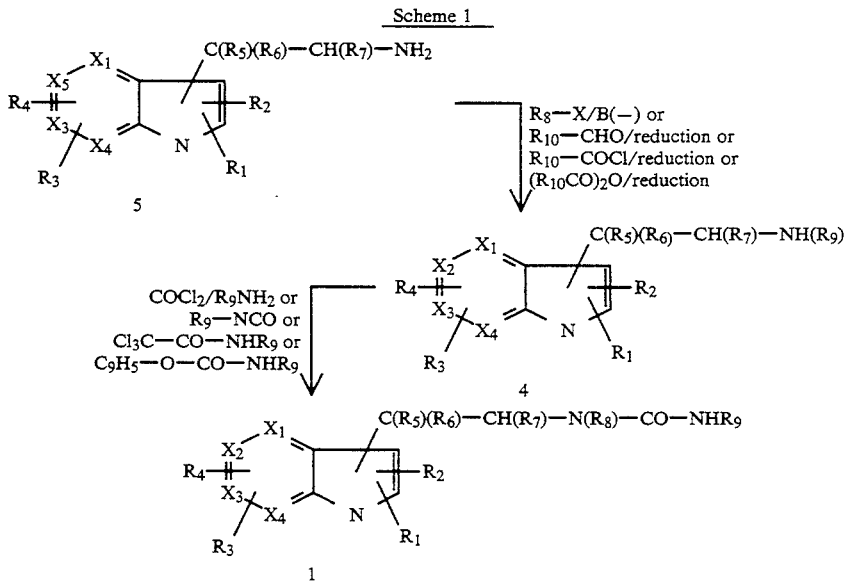

Scheme 1 a) the conversion of an aminoazaindole of general formula 5, in which $X_1$, $X_2$, $X_3$, $X_4$, $R_1$, $R_2$, $R_3$, $R_4$, $R_5$, $R_6$ and $R_7$ have the general and particular meanings already defined, to an N-substituted aminoazaindole of general formula 4; this conversion may be carried out either by alkylation with a halogenated compound of general formula $R_8$—X, in which X denotes a chlorine, bromine or iodine atom and $R_8$ has the meanings already defined, or by reaction with an aldehyde of formula $R_{10}$—CHO or an acid chloride or anhydride of general formulae $R_{10}$—COCl and $(R_{10}$—CO$)_2$O, respectively, in which formulae $R_{10}$ represents a $C_1$-$C_{11}$ alkyl radical or a phenyl radical which can bear one to three substituents chosen from halogen and $C_1$ to $C_4$ alkyl, alkoxy and alkylthio radicals, followed by reduction of the imine or amide thereby obtained, b) the aminocarbonylation of an N-substituted aminoazaindole obtained according to a) and represented by the general formula 4, in which $X_1$, $X_2$, $X_3$, $X_4$, $R_1$, $R_2$, $R_3$, $R_4$, $R_5$, $R_6$, $R_7$ and $R_8$ have the general and particular meanings explained above, by reaction with phosgene and a suitable amine of general formula $R_9$—NH$_2$, or by reaction with an isocyanate of general formula $R_9$—NCO, or a trichloroacetamide of general formula Cl$_3$C—CO—NHR$_9$, or alternatively a phenyl carbamate of general formula $C_6H_5$—O—CO—NHR$_9$, in which formulae $R_9$ has the meanings defined above.

The alkylation according to a) is carried out in the presence of a basic agent, preferably a tertiary amine such as, for example, triethylamine, in an appropriate solvent, preferably a polar solvent such as, for example, tetrahydrofuran, and generally at the refluxing temperature of the solvent used; the condensation of an aldehyde according to a) is performed in a solvent or mixture of solvents which are inert with respect to the reactants and immiscible with water; aromatic hydrocarbons, especially alkylbenzenes such as toluene or xylene, may be used, in particular, as solvents; it is possible, where appropriate, in order to facilitate the formation of the imine, to add a dehydrating agent such as, for example, para-toluenesulphonic acid; it is preferable to work at the refluxing temperature of the solvent used; the imine thereby obtained is reduced directly to the amine of general formula 4 with sodium borohydride; this reduction is performed in an appropriate solvent such as tetrahydrofuran, or an alcohol which can be, for example, methanol or alternatively ethanol, and at a temperature between room temperature and the refluxing temperature of the solvent used; the acylation according to a) is carried out in the presence of a basic agent, preferably a tertiary aliphatic amine such as, for example, triethylamine, in a solvent which is preferably tetrahydrofuran or alternatively an aromatic hydrocarbon such as, for example, benzene or an alkylbenzene such as toluene or xylene, or else a halogenated solvent such as chloroform or methylene chloride, and preferably at the boiling point of the solvent used; the amide thereby obtained is then reduced with lithium aluminium hydride in diethyl ether or tetrahydrofuran at the boiling point of the solvent used.

The condensation of an isocyanate according to b) is preferably performed in an alkane such as pentane or hexane, or alternatively in an ether such as diisopropyl ether or diethyl ether, or else, in the case of a less soluble amine, in ethyl acetate, and at the temperature best suited to obtaining the reaction, generally room temperature; the reaction according to b) employing phosgene and an amine of formula $R_9$NH$_2$ is carried out in an aromatic hydrocarbon such as, for example, toluene in the presence of a basic agent such as triethylamine and at a temperature close to room temperature; when the formation of the intermediate carbamoyl chloride is complete, it is reacted with the desired amine of formula $R_9$—NH$_2$, at a temperature between room temperature and the refluxing temperature of the solvent used; the aminocarbonylation according to b) in which a trichloroacetamide of formula Cl$_3$C—CO—NH—R$_9$ is used is carried out by heating in an aprotic polar solvent such as, for example, N,N-dimethylformamide, tetramethylurea, N-methylpyrrolidone or alternatively hexamethylphosphorotriamide, in the presence of a basic agent which is preferably an alkali metal carbonate or alkaline earth metal carbonate such as sodium or potassium carbonate, and at a temperature between room temperature and 110° C., and preferably at a temperature in the region of 110 ° C.; the aminocarbonylation according to b) in which a phenyl carbamate is used is carried out in a polar solvent such as dimethylformamide at a temperature between room temperature and the boiling point of the solvent.

The invention also relates to the intermediate compounds corresponding to the general formulae 5, 6, 7, and 8, as well as to the processes for their synthesis illustrated in scheme 2 below.

The intermediate nitriles of general formula 7 may be prepared from the appropriate azaindoles of general formula 9, in which $X_1$, $X_2$, $X_3$, $X_4$, $R_1$, $R_2$, $R_3$ and $R_4$ have the general or particular meanings already stated, according to the process described in French Patent 1,261,179 for the compounds having the acetonitrile chain at position 2 or 3, or according to the process described in Belgian Patent 659,467 for the compounds having the acetonitrile chain at position 1.

Scheme 2

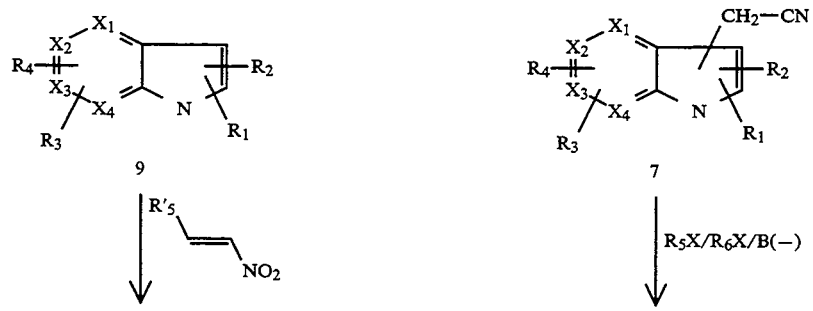

Scheme 2

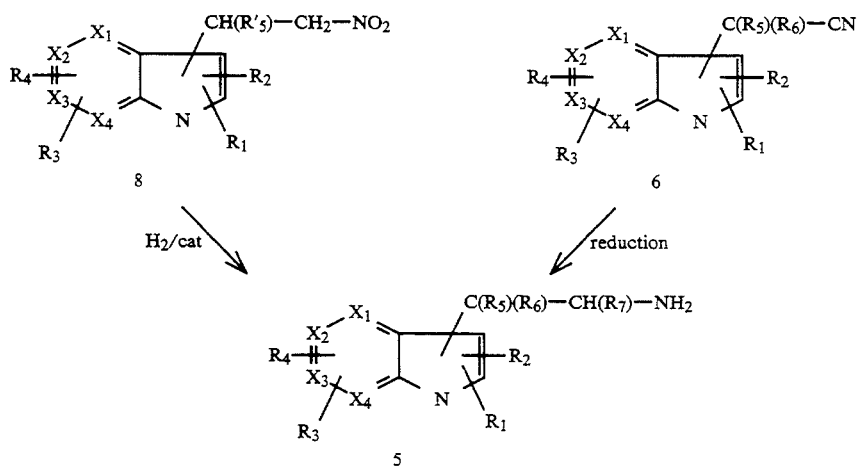

The nitriles of formula 7 can be, where appropriate, mono- or dialkylated with halides of formula $R_5$—X or $R_6$—X or with a dihalide of formula X—$(CH_2)_q$—X, in which formulae $R_5$ and $R_6$ have the general or particular meanings specified above and, where appropriate, contain a double bond, and X denotes chlorine, bromine or iodine; this alkylation reaction is carried out in the presence of a basic agent such as sodium hydride or alternatively an alkali metal amide or alkaline earth metal amide such as sodium amide or lithium diisopropylamide, in a solvent or mixture of solvents which are suitable, such as dimethylformamide or benzene or toluene or alternatively diethyl ether, and preferably at a temperature generally of between 20° and 80° C., or between −50° C. and room temperature in the special case where a lithium amide is the compound used as base.

The nitriles (6) are reduced to the amines (5); this reduction consists of a catalytic hydrogenation or alternatively a chemical reduction; the catalytic hydrogenation is performed at atmospheric pressure or at a pressure which can range up to 180 bars, in the presence of a metal catalyst such as, for example, palladium dispersed on charcoal or Raney nickel and a base which is generally sodium hydroxide pellets, ammonia or alternatively a tertiary aliphatic amine such as triethylamine, in a solvent which is compatible with hydrogen, preferably a polar solvent such as, for example, tetrahydrofuran or an alcohol such as methanol, ethanol or isopropanol; the chemical reduction is carried out preferably using lithium aluminium hydride as a reducing agent, although other agents that reduce the nitrile function can also be suitable, in a solvent customarily used with this reducing agent, such as tetrahydrofuran or diethyl ether, at a temperature between room temperature and the refluxing temperature of the solvent used, but preferably at its refluxing temperature.

Another process for obtaining the amines (5) consists in condensing the azaindoles (9) with a nitroalkene of general formula R'—CH=CH—$NO_2$, in which $R'_5$ denotes a phenyl radical which can bear halogen or $C_1$—$C_4$ alkyl, alkoxy or alkylthio substituents; this condensation, which is performed at a temperature which can be between 50° and 150° C., yields the nitro derivatives (8), which are then reduced to the amines (5); this reduction is preferably performed catalytically, at atmospheric pressure or at a pressure which can range up to 180 bars, in the presence of a metal catalyst such as, for example, palladium dispersed on charcoal or Raney nickel, in a solvent which is compatible with hydrogen, preferably a polar solvent such as, for example, tetrahydrofuran or an alcohol such as methanol, ethanol or isopropanol, at a temperature between 50° C. and its refluxing temperature.

The azaindoles of general formula 9 are prepared according to the techniques described in Russian Chemical Reviews, 1980, 49 (5 ), 428–444.

The amines of formula 4 in which $R_7$ has the meanings specified above other than hydrogen may be obtained according to scheme 3 below, according to which the ketones of general formula 10, in which $X_1$, $X_2$, $X_3$, $X_6$, $R_1$, $R_2$, $R_3$, $R_4$, $R_5$, $R_6$ and $R_7$ have the general or particular meanings already stated, by the action of a magnesium compound on the nitriles of general formula 6, in a solvent such as diethyl ether or tetrahydrofuran or in a mixture of these solvents such as a benzene/ether mixture, and at a temperature between 0° C. and its boiling point; the ketones (10) thereby obtained are then converted to the amines (4) by reaction with a primary amine of formula $R_8NH_2$, in which $R_8$ has the general meanings already stated; this reaction is performed in a solvent or solvent mixture which is inert with respect to the reactants and immiscible with water; for this purpose, it is possible to use, in particular, aromatic hydrocarbons, especially alkylbenzenes such as toluene or xylene, and, where appropriate, to add a dehydrating agent such as, for example, para-toluenesulphonic acid; it is preferable to work at the refluxing temperature of the solvent or solvent mixture used; the imines thereby obtained are then reduced in situ to the corresponding amines (5) with sodium borohydride; this reduction is performed in an appropriate solvent such as tetrahydrofuran or an alcohol which can be, for example, methanol or alternatively ethanol, and at a temperature between room temperature and the refluxing temperature of the solvent used.

Scheme 3

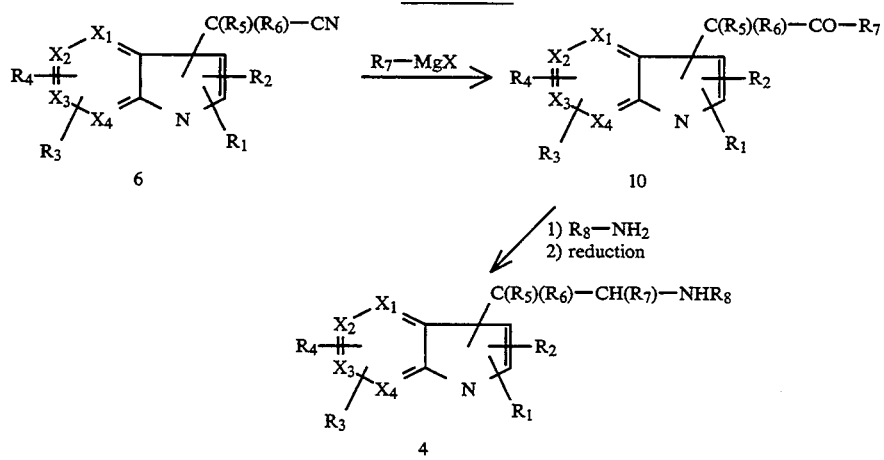

The compounds of formula 1 have the property of inhibiting acylcoenzyme A:cholesterol acyltransferase (ACAT), and exert a hypolipidaemic and antiatheromatous action.

These properties of the compounds of the invention make them especially advantageous to use as a medicinal product for the treatment or prevention of hyperlipidaemia and atherosclerosis.

The pharmacological properties of the compounds of the invention were demonstrated by the following tests:

Test A: measurement of the inhibition of aortic ACAT in vitro in rabbits; male New Zealand rabbits weighing between 2.2 and 2.5 kg, subjected beforehand for 15 days to a diet enriched with 1.25% of cholesterol, are sacrificed by cervical dislocation; the aorta is removed, dissected and homogenised in order to prepare the microsomal fraction by ultracentrifugation; these microsomes are incubated in the presence of [$^{14}$C]oleoylcoenzyme A according to the method described by P. J. GILLIES et al., Exp. and Mol. Pathol., 1986, 44, 329-339; the lipids are extracted from the incubate with a methanol/chloroform mixture and the [$^{14}$C]oleoylcholesterol is separated by TLC: the latter compound represents the measure of the ACAT activity, and the results are expressed in the form of a 50% inhibitory concentration ($IC_{50}$), representing the concentration of compound which inhibits the ACAT activity by 50%.

Test B: measurement of the hypocholesterolaemic effect in rodents; male Wistar rats weighing 200–220 g are subjected to a diet enriched with 2.5% of cholesterol for 8 days; on the last two days, they are treated orally with the test product, 24 hours and 4 hours before being sacrificed by exsanguination: the blood cholesterol level is evaluated on an aliquot fraction of serum by an automated enzymatic method. The results are expressed in the form of a 25% effective dose ($ED_{25}$) in mg per kg of animal body weight, which represents the quantity of compound which lowers the blood cholesterol level by 25%.

Test C: measurement of the inhibition of intestinal absorption of cholesterol in rats; Wistar male rats weighing 230–250 g, fasted for 24 hours, are treated simultaneously with the test product administered orally and with Triton WR-1339 administered i.v.; one hour later, they are treated again orally with [$^3$H]cholesterol; three hours later, under ether anaesthesia, 1 ml of blood is withdrawn from their retro-orbital sinus: the blood radioactivity, evaluated on 0.1 ml of serum, represents the measure of the absorption of the [$^3$H]cholesterol administered. The results are expressed in the form of a 50% effective dose ($ED_{50}$) in mg per kg of animal body weight, which represents the quantity of compound which inhibits intestinal absorption of cholesterol by 50%.

For example, for compound no. 1, an $IC_{50}$ of $160 \times 10^{-9}$ mol.l$^{-1}$ was obtained in test A, an $ED_{25}$ of 0.202 mg.kg$^{-1}$ in test B and an $ED_{50}$ of 0.056 mg.kg$^{-1}$ in test C.

The acute toxicities of the compounds of the invention were evaluated in rats and mice; it was demonstrated that, under these conditions, the compounds of the invention are especially well tolerated, since no mortality was observed at orally administered doses of more than 3200 rag. kg$^{-1}$.

These properties of the compounds of the invention make them especially advantageous to use as medicinal products, in particular for the treatment of hyperlipidaemia and atherosclerosis.

The medicinal products of the invention are characterised in that they contain an effective quantity of at least one compound of general formula 1, in combination with a pharmacologically acceptable vehicle and, where appropriate, with any other product that is acceptable from a pharmaceutical standpoint, which may be inert or physiologically active.

These medicinal products may be administered according to a wide variety of different dosage forms, for example in solid form, such as tablets, capsules including hard gelatin capsules, granules, powders, suppositories, and the like, or in the form of liquids such as syrups, elixirs or solutions for injection; in these compositions, the active principle can be, for example, mixed with one or more inert diluents such as lactose or starch and, in addition, these compounds can comprise substances other than diluents, for example lubricants such as talc or magnesium stearate; when elixirs, syrups or aqueous suspensions for oral administration are desired, the essential active ingredient may be combined therein with various sweeteners and/or flavorings, where appropriate emulsifiers and/or suspending agents, as well as diluents such as water, ethanol, propylene glycol, and various similar combinations.

These pharmaceutical compositions according to the invention generally take the form of a single dose which can contain a quantity of active principle of between 10 and 100% of their total weight, and preferably lying in the range 10 to 60%.

When the compound of the invention is used as a hypolipidaemic or antiatherosclerotic agent, the dosage adopted and the number of administrations are dependent on the patient's sex, weight and acuity of symptoms, as well as on the nature and degree of the expected therapeutic effect. In general, orally, it is preferably administered at doses of 10 to 500 mg per day in one or more portions, which corresponds for an adult of average weight 70 kg to a dose range from approximately 0.15 to 7 mg per kilo per day.

The example which follows, given without limitation, illustrates a composition of this type.

EXAMPLE

Active principle: compound no.1 .............. 50 mg
Lactose ...................................... 69 mg
Dicalcium phosphate ......................... 69 mg
Sodium carboxymethylcellulose ............. ...10 mg
Magnesium stearate ...........................2 mg The invention is illustrated by the non-limiting examples described below, in which:

all the evaporations are performed, except where otherwise stated, in a rotary evaporator under reduced pressure, the temperatures are expressed in degrees centigrade (° C.), when "room temperature" is mentioned, it means a temperature between 18° and 25° C., except where otherwise stated, the degree of progress of the reaction is monitored by thin-layer chromatography (TLC), the new compounds are, where appropriate, characterised by their physical constants: melting .point designated m.p. or boiling point designated b.p., followed, if necessary, by mention of the pressure expressed in millibars, the nuclear magnetic resonance spectra are, except where otherwise stated, proton spectra and are recorded at 60 MHz in the presence of tetramethylsilane as internal standard, the chemical shifts being stated in parts per million (ppm); the signals are described by the following abbreviations: s=singlet, d=doublet, dd=doublet of doublets, t=triplet, q=quartet, hept.-=heptet, m=multipier, the infrared spectra of the compounds are recorded using samples dispersed in potassium bromide in the case of solid compounds, or alternatively as a film in the case of liquid compounds.

EXAMPLE 1

$N^1$-[(7-Azaindol-1-yl)cyclopentylmethyl]-$N^2$-(2,6-diisopropylphenyl)urea(compound no. 1, formula 1: $R_1=R_2=R_3=R_4=R_7=R_8=H$, $R_5-R_6=-(CH_2)_4-$, $R_9=2,6$-diisopropylphenyl, $X_4=N$).

Stage 1

1-(7-Azaindol-1-yl)cyclopentanenitrile

A solution of 6.3 g (0. 029 mol) of 1,4-dibromobutane and 4.16 g of 7-azaindol-1-ylacetonitrile in 25 ml of DMF is added dropwise to a suspension of 1.4 g of NaH in 30 ml of DMF. The mixture is stirred for 4 hours at room temperature, 200 cm$^3$ of water are then added and the mixture is extracted with methylene chloride. The organic phase is then dried over sodium sulphate and thereafter filtered; the filtrate is evaporated and the residue obtained is chromatographed on 85 g of silica gel (eluant: hexane/CH$_2$Cl$_2$, then CH$_2$Cl$_2$). A liquid which crystallises is thereby obtained.

Yield=4.45 g=79%
TLC (SiO$_2$; hexane/CH$_3$CO$_2$C$_2$H$_5$, 3:1): R$_f$0.43
IR: νCN=2230 cm$^{-1}$
NMR (CDCl$_2$): 2.0 (m,4H); 2.70 (m,4H); 6.5(d, 1H); 7.2(m,2H); 7.9(dd, 1H); 8.4(dd, 1H)

Stage 2

1-(7-Azaindol-1-yl)cyclopentylmethylamine

A mixture of 4.35 g (0.0206 mol) of the nitrile obtained in stage 1 is hydrogenated for 6 hours at 70° C. in 60 ml of ethanol previously saturated with ammonia and in the presence of 2 g of Raney nickel. The mixture is filtered, the nickel is washed with 140 ml of alcohol and the solution is then evaporated to dryness. A liquid compound is thereby isolated.

Yield=3.88 g=87%
IR: νNH$_2$=3380 cm$^{-1}$
NMR (CDCl$_3$): 0.9(m,2H); 1.7(m,4H); 2.3(m,4H); 3.3(s,2H); 6.35–8.25(m,5H)

Stage 3

$N^1$-[(7-Azaindol-1-yl)cyclopentylmethyl]-$N^2$-(2,6-diisopropylphenyl)urea (compound no.1)

2.03 g (0.01 mol) of 2,6-diisopropylphenyl isocyanate are added dropwise at room temperature to a solution of 2.15 g (0.01 mol) of compound obtained in stage 2 in 50 cm$^3$ of ether, and the mixture is stirred overnight at room temperature; the precipitate obtained is then drained, washed with diisopropyl ether and thereafter with hexane and dried. Weight=2.15 g, m.p. =147°–149° C. The filtrate is evaporated to dryness and chromatographed on 46 g of silica gel (eluant: CH$_2$Cl$_2$/CH$_3$CO$_2$C$_2$H$_5$, 1:1). 1.5 q of solid are obtained, m.p. =143°–145° C.

Overall yield=90%
IR: νCO=1635 cm$^{-1}$
NMR (CDCl$_3$): 0.95(s,6H); 1.05(s,6H); 1.8(m,4H); 2.3(m,4H); 3.15(m,2H); 3.7(s,NH); 3.8(s,1H); 5.55(m, 1H); 5.8–7.8(m, 8H)

| Percentage analysis (C$_{26}$H$_{34}$N$_4$O – MW = 418.59): | | | |
|---|---|---|---|
| | C | H | N |
| % calculated: | 74.61 | 8.19 | 13.39 |
| % found: | 74.32 | 8.28 | 13.32 |

EXAMPLE 2

$N^1$-[2-(7-Azaindol-1-yl)-2-allyl-4-pentenyl ]-$N^2$-2,6-diisopropylphenyl)urea (compound no. 2, formula 1: $R_1=R_2=R_3=R_4=R_7=R_8=H$, $R_9=2,6$-diisopropylphenyl, $R_5=R_6=CH_2=CH-CH_2-$, $X_4=N$).

Stage 1

2-(7-Azaindol-1-yl)-2-allyl-4-pentenenitrile

Prepared according to the procedure of stage 1 of Example 1, using two equivalents of allyl bromide. Liquid compound.

Yield=70%.
NMR (CDCl$_3$): 3.05(dd,2H); 3.75(dd,2H); 4.86(m,6H); 6.4(d,1H); 7.04(dd,2H); 7.4(d, 1H); 7.9(d,1H); 8.25(d,2H)

Stage 2

2-(7-Azaindol-1-yl)-2-allyl-4-pentenamine 4 g of the compound of stage 1, dissolved in 40 ml of ether, are added to a suspension of 0.96 g (0.0253 tool) of LiAlH$_4$ in 100 ml of ether. The mixture is heated to reflux for 3 hours. It is cooled and 5% sodium hydroxide is added at room temperature, settling is allowed to take place, the aqueous phase is washed with ether, the ether phases are dried over sodium sulphate and filtered and the filtrate is evaporated. A liquid compound is thereby obtained.

Yield = 3.3 g = 82%.
IR: $\nu NH_2 = 3400$ cm$^{-1}$
NMR (CDCl$_3$): 1.1(d, 1H); 2.6–3.4(m,4H); 3.5(s,2H); 4.75–5.9(m,6H); 6.4(d, 1H); 7.0(dd,2H); 7.3(d, 1H); 7.85(d,1H); 8.25(d, 1H)

Stage 3

N$^1$-[2-(7-Azaindol-1-yl)-2-allyl-4-pentenyl]-N$^2$-(2,6-diisopropylphenyl)urea (compound no.2)

Prepared from the compound of stage 2, by the process described in stage 3 of Example 1.

Yield = 70%; m.p. = 118°–120° C.
IR; $\nu NH = 3207$ cm$^{-1}$; $\nu CO = 1652$ cm$^{-1}$
NMR (CDCl$_3$): 1.0(d, 12H); 2.8(d,4H); 3.25(m,2H); 4.0(d,2H); 5–5.5(m,6H); 6.0–8.0(m,10H)

| Percentage analysis (C$_{28}$H$_{36}$N$_4$O — MW = 444.62): | | | |
|---|---|---|---|
| | C | H | N |
| % calculated: | 75.64 | 8.16 | 12.60 |
| % found: | 75.65 | 8.26 | 12.36 |

EXAMPLE 3

N$^1$-[2-(7-Azaindol-1-yl)-2-allyl-4-pentenyl]-N$^2$-(4-fluoro-2-methylphenyl)urea (compound no.3, formula 1: R$_1$=R$_2$=R$_3$=R$_4$=R$_7$=R$_8$=H, R$_9$=4-fluoro-2-methylphenyl, R$_5$=R$_6$=CH$_2$=CH—CH$_2$—, X$_4$=N)

Stage 1

2,2,2-Trichloro-N-(4-fluoro-2-methylphenyl)acetamide

A solution of 9.1 g (0.05 mol) of trichloroacetyl chloride in 40 ml of dichloroethane is added at −5° C. to a solution of 6.25 g (0.05 mol) of 4-fluoro-2-methylaniline in 75 ml of dichloromethane and 3.95 g (0.05 mol) of pyridine. This solution is stirred at room temperature for one hour and then poured into ice-cold water, and the organic phase is separated after settling has taken place, washed with water and dried over sodium sulphate. It is filtered, the filtrate is evaporated and the residue is dispersed in hexane; a pink solid is thereby obtained.

Yield = 10.25 g = 75%; m.p. = 119°–121° C.
IR: $\nu CO = 1698$ cm$^{-1}$

Stage 2

N$^1$-[2-(7-Azaindol-1-yl)-2-allyl-4-pentenyl]-N$^2$-(4-fluoro-2-methylphenyl)urea (compound no.3)

A mixture of 1.2 g (1.45 mmol) of the compound obtained in stage 1, 1.58 g of K$_2$CO$_3$ and 1.13 g (1.45 mmol) of amine obtained in stage 2 of Example 2 is heated for 1 hour at 110° C. in 15 ml of DMF. The reaction mixture is poured into ice-cold water, the product is then extracted with ether and the organic phase is washed with water and dried over sodium sulphate.

After filtration and then evaporation of the filtrate, 1.4 g of a solid are obtained, which solid is chromatographed on silica (eluant: hexane/CH$_2$Cl$_2$, then CH$_2$Cl$_2$/CH$_3$CO$_2$C$_2$H$_5$, 5:1).

Yield = 0.45 g = 25%; m.p. = 150°–152° C. (diisopropyl ether)
IR: $\nu NH = 3344$ cm$^{-1}$; $\nu CO = 1632$ cm$^{-1}$
NMR (CDCl$_3$): 2.1(s,3H); 2.9(m,4H); 4(d,2H); 4.8–6(m,7H); 6.2(s,1H); 6.3–8.0(m,8H)

| Percentage analysis (C$_{23}$H$_{25}$N$_4$OF — MW = 392.48): | | | | |
|---|---|---|---|---|
| | C | H | N | F |
| % calculated: | 70.39 | 6.42 | 14.28 | 4.84 |
| % found: | 70.27 | 6.61 | 14.33 | 4.86 |

EXAMPLE 4

N$^1$-[2-(7-Azaindol-1-yl)-2-phenylethyl]-N$^2$-(2,6-diisopropylphenyl)urea (compound no. 4, formula 1 R$_1$=R$_2$=R$_3$=R$_4$=R$_5$=R$_7$=R$_8$=H, R$_9$=2,6-diisopropylphenyl, R$_6$=phenyl, X$_4$=N)

Stage 1

7-Aza-1-(2-nitro-1-phenylethyl)indole

A mixture of 2.36 g(0.02 mol) of 7-azaindole and 3.3 g of 2-phenyl-1-nitroethylene is heated to 80° C. for 5 hours. The reaction mixture is chromatographed on 112 g of silica (eluant: hexane/CH$_2$C$_{12}$, 1:1, then CH$_2$Cl$_2$, then CH$_2$Cl$_2$/CH$_3$CO$_2$C$_2$H$_5$, 5:1).

Yield = 2.4 g = 44%
NMR (CDCl$_3$): 5.15(dd, 1H); 5.7(dd, 1H); 6.4–7.5-(m,8H); 7.85(d, 1H); 8.3(d, 1H)

Stage 2

2-(7-Azaindol-1-yl)-2-phenylethylamine 2.15 g (0.008 mol) of the compound obtained in stage 1 are hydrogenated under pressure at 70° C. in 50 ml of ethanol in the presence of 1 g of Raney nickel. The reaction mixture is filtered and the filtrate is evaporated to dryness. A liquid compound is obtained.

Yield = 1.8 g = 94%
IR: $\nu NH_2 = 3367$ cm$^{-1}$
NMR (CDCl$_3$): 2.35(s,2H); 3.6(d,2H); 6–8.4(m,11H)

Stage 3

N$^1$-[2-(7-Azaindol-1-yl)-2-phenylethyl]-N$^2$-(2,6-diisopropylphenyl)urea (compound no. 4 )

Prepared from the compound of stage 2, by the process described in stage 3 of Example 1.

Yield = 65%; m.p. = 171°–173° C.
TLC: (SiO$_2$; hexane/CH$_3$CO$_2$C$_2$H$_5$, 1:1): R$_5$ = 0.6
NMR (CDCl$_3$): 0.95(d,12H); 3.0(m,2H); 4.1(m,2H); 5.1(m, 1H); 5.9(m,2H); 6.3–8.0(m,13H)

| Percentage analysis (C$_{28}$H$_{32}$N$_4$O — MW = 440.50): | | | |
|---|---|---|---|
| | C | H | N |
| % calculated: | 76.33 | 7.32 | 12.72 |
| % found: | 76.54 | 7.36 | 12.84 |

EXAMPLE 5

Using the appropriate processes of Examples 1 to 4, the compounds (see Table 1 below) of general formula in which R$_4$=R$_7$=R$_8$=H and R$_9$=2,6-diisopropylphenyl were prepared.

The abbreviations Me, Et, nBu and Ph used in the table below denote the radicals $CH_3-$, $CH_3CH_2-$, $CH_3-(CH_2)_2-CH_2-$ and $C_6H_5-$, respectively; the term $iC_3H_7$ used in the attached drawings denotes the radical $(CH_3)_2CH-$.

TABLE 1

| Compound no. | $X_1$ to $X_4$ | R1 | R2 | R3 | R5 | R6 | m.p. °C. |
|---|---|---|---|---|---|---|---|
| 5 | $X_4 = N$ | 2-H | 3-H | H | Me | Me | 140–142 |
| 6 | $X_4 = N$ | 1-Me | 2-H | H | $-(CH_2)_4-$ | | 186–188 |
| 7 | $X_2 = N$ | 2-H | 3-H | H | $-(CH_2)_4-$ | | 195.5–198 |
| 8 | $X_4 = N$ | 2-H | 3-H | H | n-Bu | H | 153–155 |
| 9 | $X_4 = N$ | 2-H | 3-Et | H | $-(CH_2)_4-$ | | 142–144 |
| 10 | $X_4 = N$ | 2-H | 3-H | H | $-(CH_2)_5-$ | | 133–135 |
| 11 | $X_4 = N$ | 2-H | 3-Ph | 6-Cl | $-(CH_2)_4-$ | | amorphous |
| 12 | $X_4 = N$ | 2-H | 3-H | H | $-CH_2-Ph$ | H | 141.5–143 |
| 13 | $X_1 = N$ | 2-H | 3-Et | H | $-(CH_2)_4-$ | | 194–196 |
| 14 | $X_4 = N$ | 2-H | 3-H | H | $-(CH_2)-O-(CH_2)_2-$ | | 152–154 |
| 15 | $X_4 = N$ | 2-H | 3-H | H | allyl | H | 153–155 |
| 16 | $X_4 = N$ | 2-Me | 3-Me | H | $-(CH_2)_4-$ | | 157–159 |
| 17 | $X_4 = N$ | 2-H | 3-$CH_2$-Ph | H | $-(CH_2)_4-$ | | 129–131 |
| 18 | $X_4 = N$ | 2-H | 3-n-Bu | H | $-(CH_2)_4-$ | | 101–103 |
| 19 | $X_4 = N$ | 2-H | 3-n-propyl | H | $-(CH_2)_4-$ | | 113–115 |
| 20 | $X_4 = N$ | 2-H | 3-isopropyl | H | $-(CH_2)_4-$ | | 134–136 |
| 21 | $X_4 = N$ | 2-H | 3-Ph | H | $-(CH_2)_4-$ | | 75–78 |
| 22 | $X_4 = N$ | 2-H | 3-H | H | Et | H | 180–182 |
| 23 | $X_4 = N$ | 2-H | 3-$CH_2$-$NME_2$ | H | $-(CH_2)_4-$ | | 128–130 |
| 24 | $X_4 = N$ | 2-H | 3-$SCH_3$ | H | $-(CH_2)_4-$ | | 119–121 |
| 25 | $X_4 = N$ | 2-H | 3-$CH_2OH$ | H | $-(CH_2)_4-$ | | amorphous |
| 26 | $X_4 = N$ | 2-H | 3-Et | 5-Cl | $-(CH_2)_4-$ | | 141–142 |
| 27 | $X_2 = N$ | 2-H | 3-H | H | $-(CH_2)_4-$ | | 184–186 |
| 28 | $X_4 = N$ | 2-H | 3-Ph | 4-Me | $-(CH_2)_4-$ | | 164–166 |
| 29 | $X_4 = N$ | 2-H | 3-Me | H | $-(CH_2)_4-$ | | 132–134 |
| 30 | $X_4 = N$ | 2-H | 3-(4-fluorophenyl) | H | $-(CH_2)_4-$ | | amorphous |
| 31 | $X_4 = N$ | 2-H | 3-Ph | H | n-Bu | H | 152–154 |
| 32 | $X_4 = N$ | 2-H | 3-(4-methoxyphenyl) | H | $-(CH_2)_4-$ | | 150–151 |
| 33 | $X_4 = N$ | 2-H | 3-$COOCH_3$ | H | $-(CH_2)_4-$ | | 190–192 |
| 34 | $X_4 = N$ | 2-H | 3-n-hexyl | H | $-(CH_2)_4-$ | | liquid |

EXAMPLE 6

$N^1$-[(7-Azaindol-1-yl)cyclopentylmethyl]-$N^2$-(2,4,6-trimethoxyphenyl)urea (compound no.35, formula 1; $R_1=R_2=R_3=R_4=R_8=H$, $R_5-R_6=-(CH_2)_4-$, $R_9=$2,4,6-trimethoxyphenyl, $X_4=N$).

Prepared from the compound of stage 2 of Example 1, by the process described in stage 2 of Example 3, using 2,2,2-trichloro-N-(2,4,6-trimethoxyphenyl)acetamide.

Yield=62%; m.p.=162°–164° C.

IR: $\nu NH=3394$ cm$^{-1}$; $\nu CO=1669$ cm$^{-1}$

NMR (CDCl$_3$): 1.5–2.8(m,8H); 3.6(s,6H); 3.75(s,6H); 4.5–5.8(m,3H); 6(s,2H); 6.25(s,1H; 6.5–7.5(m,2H); 7.5–8.1(m,2H)

| Percentage analysis ($C_{23}H_{28}N_4O_4$ — MW = 424.48): | | |
|---|---|---|
| | C | H | N |
| % calculated: | 65.08 | 6.65 | 13.20 |
| % found: | 65.30 | 6.61 | 13.33 |

EXAMPLE 7

Using the process of Example 6, the compounds (see Table 2 below) of general formula 1 in which $R_1=R_2=R_3=R_4=R_7=R_8=H$, $R_5-R_6=-(CH_2)_4-$ and $X_4=N$ were prepared.

TABLE 2

| Compound no. | $R_9$ | m.p. °C. |
|---|---|---|
| 36 | 4,6-dimethoxy-5-pyrimidinyl | 174–176 |
| 37 | 2,6-diethylphenyl | 182–184 |
| 38 | 2-isopropylphenyl | 184–186 |
| 39 | 2,4-diisopropylphenyl | 174–176 |

EXAMPLE 8

$N^1$-[(7-Azaindol-1-yl)cyclopentylmethyl]-$N^1$-benzyl-$N^2$-(2,4difluorophenyl)urea (compound no. 40, formula 1: $R_1=R_2=R_3=R_4=R_7=H$, $R_8=$benzyl, $R_9=$2,4-difluorophenyl)

Stage 1

N-Benzylidene-N-1-(7-azaindol-1-yl)cyclopentylmethylamine

A mixture of 7 g of the compound prepared in stage 2 of Example 1, 100 ml of toluene and 3.8 g of benzaldehyde is heated to reflux for 1 h 30 min, removing the water formed. The mixture is evaporated to dryness at 1 mm Hg and 9.75 g of a liquid compound are obtained.

IR: $\nu CN=1645$ cm$^{-1}$

Yield=98%

Stage 2

N-Benzyl-N-1-(7-azaindol-1-yl)cyclopentylmethylamine 1.21 g of sodium borohydride are added in small portions to a solution of 9.75 g of compound of stage 1 in 100 ml of methanol while the temperature is maintained at between 0° and 5° C. The mixture is stirred for 10 min at 0° C. and then for 2 hours at room temperature. It is poured into ice-cold water, the product is extracted with ether and the ether extract is washed with brine solution and dried over $Na_2SO_4$. The solvent is evaporated off.

IR: νNH=3340 cm$^{-1}$
Yield=8.4 g=85%
NMR (CDCl$_3$): 1–3.6(m,9H); 3.1(s,2H); 3.45(s,2H); 6.3(d, 1H); 6.7–7.5(m,7H); 7.8(dd, 1H); 8.2(dd, 1H)

Stage 3

N$^1$-[(7-Azaindol-1-yl)cyclopentylmethyl]-N$^1$-benzyl-N$^2$-(2,4-difluorophenyl)urea 1.8 g of 2,4-difluorophenyl isocyanate are added dropwise at a temperature below 20° C. to a mixture of 3.97 g of the compound of stage 2 in 50 ml of hexane. The mixture is stirred overnight and the precipitate formed is then drained, washed with hexane and recrystallised in 120 ml of diisopropyl ether.

IR: νNH=3306 cm$^{-1}$; νCO=1638 cm$^{-1}$
Yield=3.3 g=55%
TLC(SiO$_2$; hexane/AcOEt, 1:1): R$_f$=0.66
NMR (CDCl$_3$): 1.5–2.8(m,8H); 4.05(s,2H); 4.1 (s, 2H); 6.3–8.2(m,14H)

| Percentage analysis (C$_{27}$H$_{26}$F$_2$N$_4$O – MW = 460.53): | | | | |
|---|---|---|---|---|
| | C | H | N | F |
| % calculated: | 70.43 | 5.69 | 12.17 | 8.25 |
| % found: | 70.66 | 5.77 | 12.16 | 8.20 |

EXAMPLE 9

N$^1$-[(3-Bromo-7-azaindol-1-yl)cyclopentylmethyl]-N$^2$-(2,6-diisopropylphenyl)urea (compound no. 41, formula 1: R$_1$=R$_3$=R$_4$=R$_7$=R$_8$=H, R$_2$=Br, R$_5$-R$_6$=—(CH$_2$)$_4$—, R$_9$=2,6-diisopropylphenyl, X$_4$=N).

A solution of 0.76 g of bromine in 9 ml of carbon tetrachloride is added dropwise to a solution of 2 g of compound no.1 in 20 ml of chloroform; this addition is carried out at a temperature of between 0° and 10° C. The mixture is then stirred for 2 hours at room temperature and thereafter neuatralised with sodium hydroxide, the product is extracted with methylene chloride, the organic extract is washed with water, dried over Na$_2$SO$_4$ and filtered and the filtrate is evaporated to dryness. The residue obtained is recrystallised in 60 ml of diisopropyl ether.

Yield=1.1 g=46%; m.p.=137°–139° C.
TLC (SiO$_2$; hexane/AcOEt, 1:1): R$_f$=0.69
NMR(CDCl$_3$): 1(d,12H); 1.8(m,4H); 2.2(m,4H); 3.1(m,2H); 3.7(d,2H); 5.3(m,1H); 5.9(s,1H); 6.75–7.9(m,14H)

| Percentage analysis (C$_{26}$H$_{33}$Br N$_4$O – MW = 497.48): | | | | |
|---|---|---|---|---|
| | C | H | N | Br |
| % calculated: | 62.77 | 6.69 | 11.26 | 16.06 |
| % found: | 62.78 | 6.81 | 11.35 | 16.16 |

EXAMPLE 10

N$^1$-[(3-Chloro-7-azaindol-1-yl)cyclopentylmethyl]-N$^2$-(2,6-diisopropylphenyl )urea (compound no.42, formula 1: R$_1$=R$_3$=R$_4$=R$_7$=R$_8$=H, R$_2$=Cl, R$_5$R$_6$=—(CH$_2$)$_4$—, R$_9$=2,6-diisopropylphenyl, X$_4$=N).

0.93 g of N-chlorosuccinimide is added in small portions to a solution of 2.64 g of compound 1 in 75 mi of methanol while the temperature of the reaction mixture is maintained below 25° C. The mixture is then stirred for hours at room temperature, a further 0.186 g of N-chlorosuccinimide is then added and the mixture is left stirring overnight. It is taken up with water, the product is extracted with ether and the ether extract is washed with water and dried over Na$_2$SO$_4$. The crude product is purified by chromatography on silica (eluant: hexane/ethyl acetate, 3:1, then 2:1); the product obtained is recrystallised in heptane.

Yield=0.8 g=28%; m.p.=153°–155° C.
TLC (SiO2; hexane/AcOEt, 1:1): R$_f$=0.65
NMR (CDCl$_3$): 1(d,12H), 1.8(m,4H); 2.2(m,4h); 3.1(m,2H); 3.75(d,2H); 5.3(m, 1H); 6.0(s,1H); 6.8–7.9(m,14H)

| Percentage analysis (C$_{26}$H$_{33}$ClN$_4$O – MN = 453.03): | | | | |
|---|---|---|---|---|
| | C | H | N | Cl |
| % calculated: | 68.93 | 7.34 | 12.37 | 7.83 |
| % found: | 68.72 | 7.75 | 12.30 | 8.13 |

EXAMPLE 11

N$^1$-[(3-Methoxymethyl-7-azaindol-1-yl)cyclopentylmethyl]-N$^2$-(2,6-diisopropylphenyl)urea (compound no. 43, formula 1: R$_1$=R$_3$=R$_4$=R$_7$=R$_8$=H, R$_2$=—CH$_2$—O—CH$_3$, R$_5$—R$_6$=—(CH$_2$)$_4$—, R$_9$=2,6-diisopropylphenyl, X$_4$=N).

Stage 1

1-(3-Formyl-7-azaindol-1-yl)cyclopentanenitrile

A solution of 28.3 g of the nitrile prepared in stage 1 of Example 1 in 60 ml of DMF is added to a solution, cooled to 0° C., of 13.55 ml of POCl$_3$ in 70 ml of DMF while the temperature of the reaction mixture is maintained at between 1 and 3° C.; the mixture is then heated for 45 hours at 70° C., thereafter taken up with water and evaporated to dryness, and the residue obtained is dispersed in water and filtered off.

Yield=31.2 g=97%; m.p.=116°–118° C.

Stage 2

1-(3-Hydroxymethyl-7-azaindol-1-yl)cyclopentanenitrile 0.45 g of sodium borohydride is added in small portions at between 20° and 25° C. to a solution of 4.6 g of compound of stage 1 above in 80 ml of methanol. The mixture is stirred for 2 hours, 2 ml of water are then added, the resulting mixture is evaporated, the residue is taken up with dichloromethane, the dichloromethane solution is washed with water, dried over Na$_2$SO$_4$, filtered and evaporated and the residue is chromatographed on silica gel(eluant: ethyl acetate/hexane, 8:2).

Yield=3.7 g=80%, liquid

Stage 3

1-(3-Methoxymethyl-7-azaindol-1-yl)cyclopentanenitrile 3.7 g of the compound of stage 2, dissolved in 30 ml of DMF, are added to a suspension of 0.7 g of NaIl (60% suspension in oil) in 20 ml of DMF. The mixture is stirred for 30 min at room temperature and then heated for 10 min at 40° C.; 2.6 g of methyl iodide are then added and stirring is continued for 7 hours at room temperature; water is then added, the mixture is evaporated to dryness and the residue is taken up with water and extracted with ether; the organic phase is then dried over sodium sulphate and thereafter filtered; the filtrate is evaporated and the residue dispersed in diisopropyl ether.

Yield=1.9 g=46%; m.p.=78°-80° C.
TLC (SiO$_2$; CH$_3$CO$_2$C$_2$H$_5$): R$_f$=0.33

Stage 4

1-(3-Methoxymethyl-7-azaindol-1-yl)cyclopentylmethylamine

Prepared from the compound of stage 3, by the process described in stage 2 of Example 1.

Yield=99%. The product is used in the crude state in the next step.

Stage 5

N$^1$-[(3-Methoxymethyl-7-azaindol-1-yl)cyclopentylmethyl]-N$^2$-(2,6-diisopropylphenyl)urea (compound no.43)

Prepared from the compound of stage 4 above, by the process described in stage 3 of Example 1. The product obtained is chromatographed on silica gel (eluant: AcO-Et/hexane, 7:3).

Yield=94%; liquid
IR: νCO=1669 cm$^{-1}$
NMR (CDCl$_3$): 1.05(d,12H); 1.5-2.5(m,8H); 2.8-3.1(m,2H); 3.25(s,3H); 3.25-4(m,3H); 5.95(s,2H); 5.5-8(m, 8H)

| Percentage analysis (C$_{28}$H$_{38}$N$_4$O$_2$ — MW = 462.61): | | | |
|---|---|---|---|
| | C | H | N |
| % calculated: | 72.69 | 8.28 | 12.11 |
| % found: | 72.91 | 8.52 | 12.30 |

EXAMPLE 12

N$^1$-[(3-Diethylaminoethyloxymethyl-7-azaindol-1-yl)cyclopentylmethyl]-N$^2$-(2,6-diisopropylphenyl)urea
(compound no.44, formula 1:
R$_1$=R$_3$=R$_4$=R$_7$=R$_8$=H,
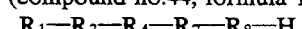
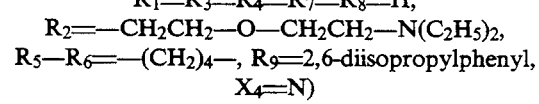
R$_5$—R$_6$=—(CH$_2$)$_4$—, R$_9$=2,6-diisopropylphenyl,
X$_4$=N)

Stage 1

1-(3-Diethylaminoethoxymethyl-7-azaindol-1-yl)cyclopentanenitrile 7 g of the compound of stage 2 of Example 11, dissolved in 80 ml of DMF, are added to a suspension of 1.16 g of NaH (60% suspension in oil) in 30 ml of DMF. The mixture is stirred for 30 rain at room temperature and then heated for 15 rain at 40 ° C.; 3.93 g of chloroethyldiethylamine in 30 ml of DMF are then added and stirring is continued for 30 hours at room temperature; the mixture is diluted with water and evaporated to dryness, the residue is taken up with water and the aqueous phase is extracted with ether. The organic phase is then dried over sodium sulphate, thereafter filtered and evaporated; the residue obtained is chromatographed on silica(eluant: ethyl acetate).

Yield=3.4 g=34%; liquid
TLC (SiO$_2$; CH$_3$CO$_2$C$_2$H$_5$): 1 spot

Stage 2

1(3-Diethylaminoethoxymethyl-7-azaindol-1-yl)cyclopentylmethylamine

Prepared from the compound of stage 1, by the process described in stage 2 of Example 1.

Yield=93%. The product is used in the crude state for the next step.

Stage 3

N$^1$-[(3-Diethylaminoethoxymethyl-7-azaindol-1-yl)cyclopentylmethyl]-N$^2$-(2,6-diisopropylphenyl)urea(compound no.44)

Prepared from the compound of stage 2 above by the process described in stage 3 of Example 1. The product obtained is chromatographed on silica gel (eluant: tetrahydrofuran).

TLC (SiO$_2$; THF): R$_f$=0.47
Yield=88%; liquid
IR: νCO=1655 cm$^{-1}$
NMR (CDCl$_3$): 0.7-2.0(m,18H); 2-2.8(m,14H); 4.0(m,7H); 4.5(s,2H); 5.0-8(m,8H)

| Percentage analysis (C$_{33}$H$_{49}$N$_5$O$_2$ — MN = 547.76): | | | |
|---|---|---|---|
| | C | H | N |
| % calculated: | 72.36 | 9.02 | 12.79 |
| % found: | 72.07 | 8.89 | 12.38 |

EXAMPLE 13

N$^1$-[(3-Ethenyl-7-azaindol-1-yl)cyclopentylmethyl]-N$^2$-(2,6-diisopropylphenyl)urea (compound no. 45, formula 1: R$_1$=R$_3$=R$_4$=R$_7$=R$_8$=H,
R$_2$=3—CH=CH$_2$, R$_5$—R$_6$=—(CH$_2$)$_4$—,
R$_9$=2,6-diisopropylphenyl, X$_4$=N)

Stage 1

1-(3-Ethenyl-7-azaindol-1-yl)cyclopentanenitrile 6.25 ml of a 1.6 N solution of n-butyllithium in hexane are added dropwise to a solution of 3.6 g of methyltriphenylphosphonium bromide in 50 ml of THF, the mixture is stirred for 15 min at room temperature and 2.4 g of the compound prepared in stage 1 of Example 11, dissolved in 25 ml of THF, are then added. The mixture is stirred for 24 hours and then heated to reflux for 4 h 30 min. It is diluted with water and then extracted with methylene chloride, the organic phase is dried over sodium sulphate and filtered and the filtrate is evaporated and chromatographed on silica (eluant: CH$_2$Cl$_2$).

Yield=1.4 g=58%
TLC (SiO$_2$; CH$_3$CO$_2$C$_2$H$_5$): R$_f$=0.94

Stage 2

1-(3-Ethenyl-7-azaindol-1-yl)cyclopentylmethylamine

Prepared from the compound of stage 1 above, by the process described in stage 2 of Example 2.

Yield=99%. The product is used in the crude state in the next step.

Stage 3

N$^1$-[(3-Ethenyl-7-azaindol-1-yl)cyclopentylmethyl]-N$^2$-(2,6-diisopropylphenyl)urea (compound no.45)

Prepared from the compound of stage 2, by the process described in stage 3 of Example 1. The compound obtained is chromatographed on silica gel(eluant: AcOEt/hexane, 7:3, then 1:1).

TLC(SiO$_2$; AcOEt/hexane, 8:2): R$_f$=0.85
Yield=70%; amorphous solid
IR: σCO=1669 cm$^{-1}$

| Percentage analysis (C$_{28}$H$_{36}$N$_4$O − MW = 444.6): | | | |
|---|---|---|---|
| | C | H | N |
| % calculated: | 75.64 | 8.16 | 12.60 |
| % found: | 75.61 | 8.24 | 12.88 |

EXAMPLE 14

N$^1$-{[3-(2-Phenylethen-1-yl)-7-azaindol-1-yl]cyclopentylmethyl}-N$^2$-(2,6-diisopropylphenyl)urea (compound no.46, formula 1: R$_1$=R$_3$=R$_4$=R$_7$=R$_8$=H, R$_2$=3—CH=CH—C$_6$H$_5$, R$_5$—R$_6$=—(CH$_2$)$_4$—, R$_9$=2,6-diisopropylphenyl, X$_4$=N)

Stage 1

1-[3-(2-Phenylethen-1-yl)-7-azaindol-1-yl]cyclopentanenitrile 10.4 ml of a 1.6 N solution of n-butyllithium in hexane are added dropwise at 10° C. to a solution of 6.5 g of benzyltriphenylphosphonium chloride in 40 ml of toluene; the mixture is stirred for 1 hour at room temperature and 4 g of the compound prepared in stage 1 of Example 11, dissolved in 60 ml of toluene, are then added. The mixture is stirred for 2 h 30 min and then heated at 60° C. for 1 h. It is then diluted with water, the organic phase is separated after settling has taken place, dried over sodium sulphate and filtered, the filtrate is evaporated and the residue is chromatographed on silica (eluant: CH$_2$Cl$_2$). The product obtained is dispersed in diisopropyl ether.

Yield=2.5 g=48%; m.p.=172°-175° C.
TLC (SiO$_2$; CH$_3$CO$_2$C$_2$H$_5$): 1 spot

Stage 2

1-[-3-(2-Phenylethen-1-yl)-7-azaindol-1-yl]cyclopentylmethylamine

Prepared from the compound of stage 1, by the process described in stage 2 of Example 2.

Yield=99%. The product is used in the crude state for the next step.

Stage 3

N$^1$-{[3-(2-phenylethen-1-yl)-7-azaindol-1-yl]cyclopentylmethyl}-N$^2$-(2,6-diisopropylphenyl)urea (compound no.46).

Prepared from the compound of stage 2, by the process described in stage 3 of Example 1. The compound obtained is chromatographed on silica gel (eluant: AcOEt/hexane, 9:1, then 1:1).

TLC (SiO$_2$; AcOEt): R$_f$=0.85
Yield=15%; amorphous solid
IR: νCO=1669 cm$^{-1}$

| Percentage analysis (C$_{34}$H$_{40}$N$_4$O + ½H$_2$O − MN = 532.69): | | | |
|---|---|---|---|
| | C | H | N |
| % calculated: | 77.09 | 7.80 | 10.58 |
| % found: | 77.30 | 7.80 | 10.42 |

EXAMPLE 15

N$^1$-{[3-(2-Methoxycarbonylethen-1-yl)-7-azaindol-1-yl]cyclopentylmethyl}-N$^2$-(2,6-diisopropylphenyl)urea (compound no.47, formula 1: R$_1$=R$_3$=R$_4$=R$_7$=R$_8$=H, R$_2$=—CH=CHCOOCH$_3$, R$_5$—R$_6$=—(CH$_2$)$_4$—, R$_9$=2,6-diisopropylphenyl, X$_4$=N)

A mixture of 5 ml of methyl acrylate, 25 ml of DMF, 25 ml of triethylamine, 0.05 g of palladium acetate, 0.18 g of tritolylphosphine and 5 g of compound 41 is heated to reflux. After 6 hours of heating, a further 0.05 g of palladium acetate and 0.18 g of tritolylphosphine are added, the mixture is then heated to reflux for 6 hours, then evaporated to dryness and diluted with water and the product is extracted with methylene chloride; the organic phase is washed with water, dried over sodium sulphate and filtered, the filtrate is evaporated and the residue is chromatographed on silica gel (eluant: ethyl acetate/heptane, 2:3). The product obtained is dispersed in diisopropyl ether, filtered off and purified by chromatography under moderate pressure (eluant: ethyl acetate/heptane, 1:1). The compound obtained is dispersed in diisopropyl ether.

Yield=0.4 g=7.9%; m.p.=120°-122° C.
IR: νCO=1702 and 1667 cm$^{-1}$
NMR (CDCl$_3$): 1.0(d,12H); 1.8-2.25(m, 8H); 3.8 (s+m, 5H); 5.1(t,1H); 6.0(s,1H); 6.2(d, 1H); 6.9-8.1(m,8H)

| Percentage analysis (C$_{30}$H$_{38}$N$_4$O$_3$ − MW = 502.64): | | | |
|---|---|---|---|
| | C | H | N |
| % calculated: | 71.68 | 7.62 | 11.15 |
| % found: | 71.62 | 7.75 | 11.15 |

EXAMPLE 16

N$^1$-[(3-Piperidino-7-azaindol-1-yl)cyclopentylmethyl]-N$^2$-2,6-diisopropylphenyl) urea(composed no. 48, formula 1: R$_1$=R$_3$=R$_4$=R$_7$=R$_8$=H, R$_2$=piperidino, R$_5$—R$_6$=—(CH$_2$)$_4$—, R$_9$=2,6-diisopropylphenyl, X$_4$=N)

Stage 1

1-(3-Bromo-7-azaindol-1-yl)cyclopentanenitrile

Prepared from the compound prepared in stage 1 of Example 1, according to the procedure of Example 9.
Yield=77%; m.p.=143°-145° C.

Stage 2

1-(3-Piperidino-7-azaindol-1-yl)cyclopentylmethylamine 2.9 g of the compound of stage 1 in 30 ml of piperidine are heated in an autoclave at 205° C. for hours. The mixture is then heated for 4 hours at 220° C. It is diluted with water, the product is extracted with ether, the organic phase is washed with water, dried over sodium sulphate and filtered and the filtrate is evaporated. The residue is chromatographed on silica (eluant: methylene chloride, then ethyl acetate).

Yield=0.4 g=13%
IR: νCN=2228 cm$^{-1}$
NMR (CDCl$_3$): 1.5-2.2(m,10H); 2.5-3.1(m, 8H); 6.6(s,1H); 6.95-4(m, 1H); 5.9(dd, 1H); 8.3(dd, 1H)

Stage 3

1-(3-Piperidino-7-azaindol-1-yl)cyclopentylmethylamine

Prepared from the compound of stage 2 above, by the process described in stage 2 of Example 2.

TLC (SiO$_2$; EtOH/CH$_2$Cl$_2$): 1 spot
IR: $\nu$NH$_2$=3370 and 3300 cm$^{-1}$

Stage 4

N$^1$-[(3-piperidino-7-azaindol-1-yl)cyclopentylmethyl]-N$^2$-(2,6-diisopropylphenyl)urea (compound no.48)

Prepared from the compound of stage 3 above, by the process described in stage 3 of Example 1. The compound obtained is chromatographed on silica gel (eluant: AcOEt/heptane, 1:1, then AcOEt/heptane, 45:55).

Yield=43%; amorphous solid
IR: $\nu$CO=1668 cm$^{-1}$
NMR (CDCl$_3$): 1.05(d,12H); 1.7–2.2(m,14H); 6.9(m,4H); 3.1(m,2H); 3.75(d,2H); 5.8(q,2H); 6.55(s,1H); 6.3–7.3(m,4H); 7.45(dd,1H); 7.75(dd, 1H)

| Percentage analysis (C$_{31}$H$_{43}$N$_5$O — MN = 501.69): | | | |
|---|---|---|---|
| | C | H | N |
| % calculated | 74.21 | 8.64 | 13.96 |
| % found: | 74.19 | 8.73 | 13.86 |

EXAMPLE 17

N$^1$-[(7-Azaindol-1-yl)cyclopentylmethyl]-N$^2$-(2,6-diisopropylphenyl)urea hydrochloride (compound no. 49, formula 1: R$_1$=R$_2$=R$_3$=R$_4$=R$_7$=R$_8$=H, R$_5$—R$_6$=—(CH$_2$)$_4$—, R$_9$=2,6-diisopropylphenyl, X$_4$=N)

1.05 g of compound 1 are dissolved in 25 ml of ethanol, and 1 ml of a 6 N solution of HCl in ethanol is added. After 48 hours' stirring, the mixture is evaporated, the residue is taken up with 25 ml of ethyl acetate and the mixture is heated to reflux, cooled and filtered.

Yield=0.8 g=72%; m.p.=178°–180° C.
IR: $\nu$NH=3222, 3263 and 3333 cm$^{-1}$; $\nu$CO=1685 cm$^{-1}$
NMR (CDCl$_3$): 1.05(d,12H); 1.8–2.45(m, 8H); 3(m,2H); 3.9(s,2H); 6–8(m,8H)

| Percentage analysis (C$_{26}$H$_{35}$ClN$_4$O — MW = 455.03): | | | |
|---|---|---|---|
| | C | H | N | Cl |
| % calculated: | 68.63 | 7.75 | 12.31 | 7.79 |
| % found: | 68.97 | 7.88 | 12.12 | 7.86 |

EXAMPLE 18

N$^1$-[(7-Azaindol-1-yl)cyclopentylmethyl]-N$^1$-benzyl-N$^2$-(2,6-(diisopropylphenyl)urea (compound no.50, formula 1: R$_1$=R$_2$=R$_3$=R$_4$=R$_7$=H, R$_5$—R$_6$=—(CH$_2$)$_4$—, R$_8$=benzyl, R$_9$=2,6-diisopropylphenyl)

Prepared from the compound prepared in stage 2 of Example 8, by the process described in stage 3 of Example 1. The compound obtained is chromatographed on silica gel (eluant: CH$_2$Cl$_2$/hexane, 1:1).

Yield=53%; m.p.=70°–72° C.
IR: $\nu$CO=1651 cm$^{-1}$
NMR (CDCl$_3$): 1.1(d, 12H); 1.8(m,4H); 2.5(m,4H); 3.0(m,2H); 4.0(s,3H); 4.1(s,2H); 6.4–8.1(m,13H)

| Percentage analysis (C$_{33}$H$_{40}$N$_4$O — MW = 508.71): | | | |
|---|---|---|---|
| | C | H | N |
| % calculated: | 77.92 | 7.93 | 11.01 |
| % found: | 78.18 | 8.05 | 11.16 |

EXAMPLE 19

N$^1$-[2-(3-Ethyl-7-azaindol-1-yl)hexyl]-N$^2$-(2,6-diisopropylphenyl)urea hydrochloride (compound no.51, formula 1: R$_1$=Et, R$_2$=R$_3$=R$_4$=R$_6$=R$_7$=R$_8$=H, R$_5$=Bu, R$_9$=2,6-diisopropylphenyl)

The corresponding base is prepared from 2-(3-ethyl-7-azaindol-1-yl)hexanamine by the process described in stage 3 of Example 1. Its hydrochloride is prepared according to the process of Example 17.

Yield=46%; m.p.=130°–133° C.
IR: $\nu$CO=1680 cm$^{-1}$

| Percentage analysis (C$_{28}$H$_{41}$NCl$_4$O — MW = 485.12): | | | |
|---|---|---|---|
| | C | H | N | Cl |
| % calculated | 69.33 | 8.52 | 11.55 | 7.31 |
| % found: | 69.12 | 8.62 | 11.42 | 7.27 |

I claim:

1. A compound selected from the group consisting of compounds of the formula I,

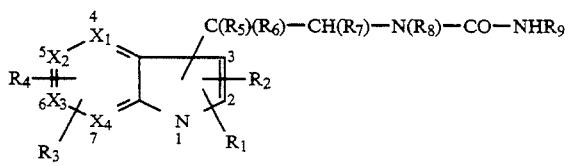

wherein
one of the groups X$_1$ to X$_4$ is nitrogen and the others are CH;

R$_1$ and R$_2$, which may be located at position 1, 2 or 3 of azaindole, each are selected from hydrogen, linear or branched C$_1$ to C$_{12}$ alkyl or C$_2$ to C$_6$ alkenyl optionally substituted at the $\omega$ position with a group selected from carboxyl, C$_1$ to C$_3$ alkyl carboxylate and phenyl; R$_1$ and R$_2$ can also be C$_3$ to C$_8$ cycloalkyl or C$_3$ to C$_8$ cycloalkenyl or, when they are at position 2 or 3 of azaindole, halogen, or C$_1$ to C$_4$ alkylthio; R$_1$ and R$_2$ can also be phenyl or benzyl, unsubstituted or having one to three substituents selected from halogen and C$_1$ to C$_4$ alkyl, C$_1$ to C$_4$ alkoxy and C$_1$ to C$_4$ alkylthio, or thienyl or pyridyl which can optionally have a substituent selected from halogen and C$_1$ to C$_4$ alkyl and C$_1$ to C$_4$ alkoxy; one of R$_1$ and R$_2$ can also be selected from hydroxymethyl, (C$_1$ to C$_4$ alkoxy)methyl, N,N-di(C$_1$ to C$_4$ alkyl)amino(C$_1$ to C$_4$ alkyl)oxymethyl, piperidino, carboxyl and C$_1$ to C$_3$ alkyl carboxylate and the other hydrogen;

R$_3$ and R$_4$, which may be located on the ventricles 4, 5, 6 of 7 of azaindole provided that these vertices embody carbon, each are selected from hydrogen, halogen, C$_1$ to C$_6$ alkyl, C$_1$ to C$_4$ alkoxy, C$_1$ to C$_6$ alkylthio or C$_3$ to C$_8$ cycloalkyl;

—C($R_5$)($R_6$)—CH($R_7$)—N($R_8$)—CO—NH—$R_9$ may be attached to the verticles 1, 2, or 3 of azaindole, on the understanding that, when nitrogen at position 1 of azaindole is not substituted with one of $R_1$, $R_2$ or —C($R_5$)($R_6$)—CH($R_7$)—N($R_8$)—CO—NH—$R_9$, it bears hydrogen;

$R_5$ and $R_6$ are each selected from hydrogen, $C_1$ to $C_{12}$ alkyl, $C_2$ to $C_6$ alkenyl, $C_3$ to $C_8$ cycloalkyl, $C_3$ to $C_8$ cycloalkenyl, $C_2$ to $C_{12}$ alkoxyalkyl, $C_2$ to $C_{12}$ alkyl-thioalkyl, or alternatively $R_5$ and $R_6$ together form and alkylene chain of the formula —$(CH_2)_p$— optionally substituted with one or two $C_1$ to $C_4$ alkyl and in which p can assume the values 3 to 7, or an alkyleneoxyalkylene chain of the formula —$(CH_2)_x$—O—$(CH_2)$—$_y$, in which x and y can independently assume the value 1 or 2;

$R_7$ is selected from hydrogen, $C_2$ to $C_6$ alkyl and $C_3$ to $C_8$ cycloalkyl;

one of the substituents $R_5$ to $R_7$ can also be phenyl or benzyl, unsubstituted or having one to three substituents selected from halogen, $C_1$ to $C_4$ alkyl, alkoxy and alkylthio;

$R_8$ is selected from hydrogen, $C_1$ to $C_{12}$ alkyl, $C_3$ to $C_8$ cycloalkyl and benzyl which is unsubstituted or bears 1 to 3 substituents selected from halogen, $C_1$ to $C_4$ alkyl, alkoxy and alkylthio;

$R_9$ is pyrimidyl or phenyl, unsubstituted or bearing one to three substituents selected from halogen and $C_1$ to $C_4$ alkyl, $C_1$ to $C_4$ alkoxy and $C_1$ to $C_4$ alkylthio.

2. A compound as claimed in claim 1, wherein one of the groups $X_1$ to $X_4$ is nitrogen and the others are CH;

$R_1$ and $R_2$, which may be located at position 1, 2 or 3 of azaindole, each are selected from hydrogen or, linear or branched to $C_1$ to $C_{12}$ alkyl, $C_2$ to $C_6$ alkenyl, $C_3$ to $C_8$ cycloalkyl, $C_3$ to $C_8$ cycloalkenyl, $C_1$ to $C_6$ alkylthio, or, when they are at position 2 to 3 of azaindole, halogen; $R_1$ and $R_2$ can also be phenyl or benzyl, unsubstituted or having one to three substituents selected from halogen, $C_1$ to $C_4$ alkyl, alkoxy and alkylthio;

$R_3$ and $R_4$, which may be located on the vertices 4, 5, 6 or 7 of azaindole provided that these vertices embody carbon, each are selected from hydrogen, halogen, $C_1$ to $C_6$ alkyl, $C_1$ to $C_6$ alkoxy, $C_1$ to $C_6$ alkylthio and $C_3$ to $C_8$ cycloalkyl;

—C($R_5$)($R_6$)—CH($R_7$)—N($R_8$)—CO—NH—$R_9$ may be attached to the vertices 1, 2 or 3 of azaindole, on the understanding that, when nitrogen at position 1 of azaindole is not substituted with one of $R_1$, $R_2$ or —C($R_5$)($R_6$)—CH($R_7$)—N($R_8$)—CO—NH—$R_9$, it bears hydrogen;

$R_5$ and $R_6$ are each selected from hydrogen, $C_1$ to $C_{12}$ alkyl, $C_2$ to $C_6$ alkenyl, $C_3$ to $C_8$ cycloalkyl or $C_3$ to $C_8$ cycloalkenyl, $C_2$ to $C_{12}$ alkoxyalkyl or $C_2$ to $C_{12}$ alkylthioalkyl, or alternatively $R_5$ and $R_6$, together form an alkylene chain of the formula —$(CH_2)_p$- optionally substituted with one or two $C_1$ to $C_4$ alkyl and in which p can assume the values 3 to 7, or an alkyleneoxyalkylene chain of the formula —$(CH_2)_x$—O$(CH_2)$—$_y$, in which x and y can independently assume the value 1 or 2;

$R_7$ is selected from hydrogen, $C_1$ to $C_6$ alkyl and $C_3$ to $C_8$ cycloalkyl;

one of the substituents $R_6$ and $R_7$ can also be phenyl or benzyl, unsubstituted or having one to three substituents selected from halogen, $C_1$ to $C_4$ alkyl, $C_1$ to $C_4$ alkoxy and $C_1$ to $C_4$ alkylthio;

$R_8$ is selected from hydrogen, $C_1$ to $C_{12}$ alkyl, $C_3$ to $C_8$ cycloalkyl and $C_3$ to $C_8$ benzyl which is unsubstituted or bears 1 to 3 substituents selected from halogen, $C_1$ to $C_4$ alkyl, $C_1$ to $C_4$ alkoxy and alkylthio;

$R_9$ is pyrimidyl or phenyl, unsubstituted or bearing one to three substituents selected from halogen, $C_1$ to $C_4$ alkyl, alkoxy and alkylthio.

3. A compound as claimed in claim 1, wherein $R_1$ and $R_2$ independently are selected from hydrogen, halogen, alkyl, phenyl and benzyl; $R_3$ and $R_4$ are selected from hydrogen, halogen, $C_1$ to $C_6$ alkyl and $C_1$ to $C_6$ alkoxy; $R_5$ and $R_6$ form hydrogen, halogen, $C_1$ to $C_6$ alkyl or alkoxy, $C_2$ to $C_6$ alkenyl, or together form a $C_4$ alkylene chain; $R_7$ is hydrogen; $R_8$ is selected from hydrogen and $C_1$ to $C_8$ alkyl, and $R_9$ is phenyl, unsubstituted or having one to three substituents selected from halogen, $C_1$ to $C_4$ alkyl and alkoxy.

4. A compound selected from the group consisting of:

$N^1$-[1-(7-azaindol-1-yl)cyclopentylmethyl]-$N^2$-(2,6-diisopropylphenyl)urea;

$N^1$-[2-(7-azaindol-1-yl)-2-alkyl-4-pentenyl]-$N^2$-(2,6-diisopropylphenyl)urea;

$N^1$-[2(7-azaindol-1-yl)-2-allyl-4-pentenyl]-$N^2$-(4-fluoro-2-methylphenyl)urea;

$N^1$-[2-(7-azaindol-1-yl)-2-phenethyl]-$N^2$-(2,6-diisopropylphenyl)urea;

$N^1$-[2-(7-azaindol-1-yl)-2-methyl-propyl]-$N^2$-(2,6-diisopropylphenyl)urea;

$N^1$-[(1-methyl-7-azaindol-3-yl)cyclopentylmethyl]-$N^2$-(2,6-diisopropylphenyl)urea;

$N^1$-[(5-azaindolyl-1-)cyclopentylmethyl]-$N^2$-(2,6-diisopropylphenyl)urea;

$N^1$-[2-(7-azaindol-1-yl)hexyl]-$N^2$-(2,6-diisopropylphenyl)urea;

$N^1$-[1-(3-ethyl-7-azaindol-1-yl)cyclopentylmethyl]-$N^2$-(2,6-diisopropylphenyl)urea;

$N^1$-[1-(7-azaindol-1-yl)cyclohexylmethyl]-$N^2$-(2,6-diisopropylphenyl)urea;

$N^1$-[1-(6-chloro-3-phenyl-7-azaindol-1-yl)cyclopentylmethyl]-$N^2$-(2,6-diisopropylphenyl)urea;

$N^1$-[2(7-azaindol-1-yl)-3-phenylpropyl]-$N^2$-(2,6-diisopropylphenyl)urea;

$N^1$-[1-(3-ethyl-4-azaindol-1-yl)cyclopentylmethyl]-$N^2$-(2,6-diisopropylphenyl)urea;

$N^1$-[4-(7azaindol-1-yl)-4-pyranylmethyl]-$N^2$-(2,6-diisopropylphenyl)urea;

$N^1$-[4-(7-azaindol-1-yl)-1-penten-5-yl]-$N^2$-(2,6-diisopropylphenyl)urea;

$N^1$-[1-(2,3-dimethyl-7-azaindol-1-yl)cyclopentylmethyl]-$N^2$-(2,6-diisopropylphenyl)urea;

$N^1$-[1-(3-benzyl-7-azaindol-1-yl)cyclopentylmethyl]-$N^2$-(2,6-diisopropylphenyl)urea;

$N^1$-[1-(3-butyl-7-azaindol-1-yl)cyclopentylmethyl]-$N^2$-(2,6-diisopropylphenyl)urea;

$N^1$[1-(3-propyl-azaindol-1-yl)cyclopentylmethyl]-$N^2$-[2,6-diisopropylphenyl)urea;

$N^1$-[1-(3-isopropyl-7-azaindol-1-yl)cyclopentylmethyl]-$N^2$-(2,6-diisopropylphenyl)urea;

$N^1$-[1-(3-phenyl-7-azaindol-1-yl)cyclopentylmethyl]-$N^2$-(2,6-diisopropylphenyl)urea;

$N^1$-[2-(7-azaindol-1-yl)butyl]-$N^2$-(2,6-diisopropylphenyl)urea;

$N^1$-[1-(3-dimethylaminomethyl-7-azaindol-1-yl)cyclopentylmethyl]-$N^2$-(2,6-diisopropylphenyl)urea;

$N^1$-[1-(3-methylthio-7-azaindol-1-yl)cyclopentylmethyl]-$N^2$-(2,6-diisopropylphenyl]urea;

$N^1$-[1-(3-hydroxymethyl-7-azaindol-1-yl)cyclopentylmethyl]-$N^2$-(2,6-diisopropylphenyl)urea;
$N^1$-[1-(5-chloro-3-ethyl-7-azaindol-1-yl)cyclopentylmethyl]-$N^2$-(2,6-diisopropylphenyl)urea;
$N^1$-[1-(6-azaindol-1-yl)cyclopentylmethyl]-$N^2$-(2,6-diisopropylphenyl)urea;
$N^1$-[1-(4-methyl-3-phenyl-7-azaindol-1-yl)cyclopentylmethyl]-$N^2$-(2,6-diisopropylphenyl)urea;
$N^1$-[1-(3-methyl-7-azaindol-1-yl)cyclopentylmethyl]-$N^2$-(2,6-diisopropylphenyl)urea;
$N^1$-{1-[3-(4-fluorophenyl)-7-azaindol-1-yl]cyclopentylmethyl}-$N^2$-(2,6-diisopropylphenyl)urea;
$N^1$-[2-(3-phenyl-7-azaindol-1-yl)hexyl]-$N^2$-(2,6-diisopropylphenyl)urea;
$N^1$-{1-[3-(4-methoxyphenyl)-7-azaindol-1-yl]cyclopentylmethyl}-$N^2$-(2,6-diisopropylphenyl)urea;
$N^1$-[1-(3-methoxycarbonyl-7-azaindol-1-yl)cyclopentylmethyl]$N^2$-(2,6-diisopropylphenyl)urea;
$N^1$-[1-(3-hexyl-7-azaindol-1-yl)cyclopentylmethyl]-$N^2$-(2,6-diisopropylphenyl)urea;
$N^1$-[1-(7-azaindol-1-yl)cyclopentylmethyl]-$N^2$-(2,4,6-trimethoxyphenyl)urea;
$N^1$-[1-(7-azaindol-1-yl)cyclopentylmethyl]-$N^2$-(4,6-dimethoxy-5-pyrimidinyl)urea;
$N^1$-[1-(7-azaindol-1-yl)cyclopentylmethyl]-$N^2$-(2,6-diethylphenyl)urea;
$N^1$-[1-(7-azaindol-1-yl)cyclopentylmethyl]-$N^2$-(2-isopropylphenyl)urea;
$N^1$-[1-(7-azaindol-1-yl)cyclopentylmethyl]-$N^2$-(2,4-diisopropylphenyl)urea;
$N^1$-[1-(7-azaindol-1-yl)cyclopentylmethyl]-$N^1$-benzyl-$N^2$-(2,4-difluorophenyl)urea;
$N^1$-[1-(3-bromo-7-azaindol-1-yl)cyclpentylmethyl]-$N^2$-(2,6-diisopropylphenyl)urea;
$N^1$-[1-(3-chloro-7-azaindol-1-yl)cyclopentylmethyl]-$N^2$-(2,6-diisopropylphenyl)urea;
$N^1$-[1-(3-methoxymethyl-7-azaindol-1-yl)cyclopentylmethyl]-$N^2$-(2,6-diisopropylphenyl)urea;
$N^1$-{1-[3-(2-diethylaminoethoxymethyl)-7-azaindol-1-yl]cyclopentylmethyl}-$N^2$-(2,6-diisopropylphenyl)urea;
$N^1$-[1-(3-ethenyl-7-azaindol-1-yl)cyclopentylmethyl]-$N^2$-(2,6-diisopropylphenyl)urea;
$N^1$-{1-[3-(2-phenylethen-1-yl)-7-azaindol-1-yl]cyclopentylmethyl}-$N^2$-(2,6-diisopropylphenyl)urea;
$N^1$-{1-[3-(2-methoxycarbonylethen-1-yl)-7-azaindol-1-yl]cyclopentylmethyl}-$N^2$-(2,6-diisopropylphenyl)urea;
$N^1$-[1-(3-piperidino-7-azaindol-1-yl)cyclopentylmethyl]-$N^2$-(2,6-diisopropylphenyl)urea;
$N^1$-[(7-azaindol-1-yl)cyclopentylmethyl]-$N^2$-(2,6-diisopropylpenyl)urea hydrochloride;
$N^1$-[1-(7-azaindol-1-yl)cyclopentylmethyl]-$N^1$-benzyl-$N^2$-(2,6-diisopropylphenyl)urea;
$N^1$-[2-(3-ethyl-7-azaindol-1-yl)hexyl]-$N^2$-(2,6-diisopropylphenyl)urea hydrochloride.

5. An intermediate compound in the preparation of the compounds of the general formula I as claimed in claim 1, represented by the following general formulae 4 and 8:

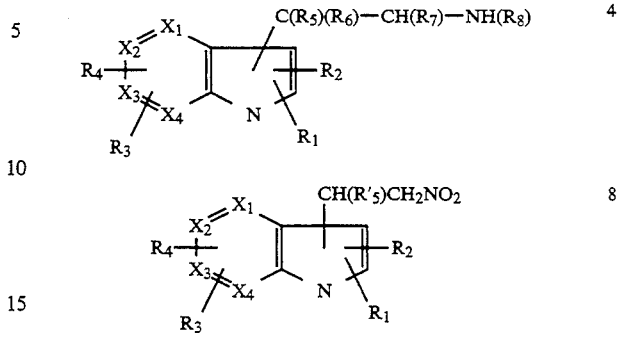

wherein the substituents $R_1$ to $R_7$ and $X_1$ to $X_4$ have the meanings claimed in claim 1, $R'_5$ is phenyl which can bear a substituent selected from halogen, $C_1$–$C_4$ alkyl, $C_1$–$C_4$ alkoxy or $C_1$–$C_4$ alkylthio, and $R_8$ has the meanings claimed in claim 1 except for hydrogen.

6. A therapeutic composition having a hypolipidaemic activity containing an effective amount of at least one compound selected from the compounds of the formula 1 as claimed in claim 1, in admixture with a therapeutic acceptable excipient, said amount being effective on the hypolipidaemic activity.

7. A therapeutic composition having an antiatherosclerotic activity containing an effective amount of at least one compound selected from the compounds of the formula 1 as claimed in claim 1, in admixture with a therapeutic acceptable excipient, said amount being effective on the anti-atherosclerotic activity.

8. A therapeutic composition having an inhibitory activity with respect to vascular and intestinal ACAT activity containing an effective amount of at least one compound selected from the compounds of the formula 1 as claimed in claim 1, in admixture with a therapeutic acceptable excipient, said amount being effective to inhibit the vascular and intestinal ACAT activity.

9. Therapeutic composition as claimed in claim 6, consisting in the form of a dosage unit, in which each dosage unit contains from 10 to 500 mg of active principle mixed with a therapeutic acceptable excipient.

10. Therapeutic composition as claimed in claim 7, consisting in the form of a dosage unit, in which each dosage unit contains from 10 to 500 mg of active principle mixed with a therapeutic acceptable excipient.

11. Method for the treatment of hyperlipidaemia which comprises administering to a human in need thereof an effective amount of a compound as claimed in claim 1, said amount being effective to inhibit said hyperlipidaemia.

12. Method for the treatment of atherosclerosis which comprises administering to a human in need thereof an effective amount of a compound as claimed in claim 1, said amount being effective to inhibit said atherosclerosis.

* * * * *